United States Patent
Macielag et al.

(10) Patent No.: US 6,323,215 B1
(45) Date of Patent: Nov. 27, 2001

(54) NEUROTROPHIC TETRAHYDROISOQUINOLINES AND TETRAHYDROTHIENOPYRIDINES, AND RELATED COMPOSITIONS AND METHODS

(75) Inventors: Mark Macielag, Branchburg; Zhihua Sui, Flemingtn; Shawn Walsh, Somerville, all of NJ (US); Boyo Zhao, Lansdale, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/592,530

(22) Filed: Jun. 12, 2000

Related U.S. Application Data

(60) Provisional application No. 60/143,098, filed on Jul. 9, 1999.

(51) Int. Cl.[7] .................. A61K 31/4365; A61K 31/472; A61K 31/4725; C07D 401/12; C07D 217/26; C07D 495/04
(52) U.S. Cl. .......................... 514/301; 514/307; 546/114; 546/145; 546/146; 546/147
(58) Field of Search .................... 546/114, 147, 546/146, 145; 514/301, 307

(56) References Cited

U.S. PATENT DOCUMENTS

| | | | |
|---|---|---|---|
| 4,147,787 | 4/1979 | Maffrand | 424/256 |
| 5,294,603 | 3/1994 | Rinehart | 514/10 |
| 5,461,146 | 10/1995 | Lewis et al. | 540/545 |
| 5,614,547 | 3/1997 | Hamilton et al. | 514/423 |
| 5,621,101 | 4/1997 | Lewis et al. | 540/545 |
| 5,696,135 | 12/1997 | Steiner et al. | 514/317 |
| 5,721,256 | 2/1998 | Hamilton et al. | 514/330 |
| 5,756,494 | 5/1998 | Lewis et al. | 514/211.08 |
| 5,795,908 | 8/1998 | Hamilton et al. | 514/423 |
| 5,798,355 | 8/1998 | Steiner et al. | 514/248 |
| 5,801,187 | 9/1998 | Li et al. | 514/365 |
| 5,801,197 | 9/1998 | Steiner et al. | 514/548 |
| 5,811,434 * | 9/1998 | Zelle | 514/307 |
| 6,037,370 * | 3/2000 | Armistead | 514/533 |

FOREIGN PATENT DOCUMENTS

| | | |
|---|---|---|
| 046953 | 6/1981 | (EP) . |
| 260 118 | 4/1991 | (EP) . |
| WO 92/19593 | 11/1992 | (WO) . |
| WO94/02488 | 2/1994 | (WO) . |
| WO94/07858 | 4/1994 | (WO) . |
| WO96/13506 | 5/1996 | (WO) . |
| WO96/36630 | 11/1996 | (WO) . |
| WO96/40140 | 12/1996 | (WO) . |
| WO96/40633 | 12/1996 | (WO) . |
| WO97/16190 | 5/1997 | (WO) . |
| WO98/13343 | 4/1998 | (WO) . |
| WO98/13355 | 4/1998 | (WO) . |
| WO98/20892 | 5/1998 | (WO) . |
| WO98/25950 | 6/1998 | (WO) . |
| WO98/29116 | 7/1998 | (WO) . |
| WO98/29117 | 7/1998 | (WO) . |
| WO98/37882 | 9/1998 | (WO) . |
| WO98/37885 | 9/1998 | (WO) . |
| WO99/45006 | 9/1999 | (WO) . |
| 964852 | 6/1996 | (ZA) . |

OTHER PUBLICATIONS

Brinton, R.D. and Yamazaki, R.S., *Pharm. Res.*, 1998, 15, 386–398.
Pahwa, R. and Koller, W.C., *Drugs Today*, 1998, 34, 95–105.
Louvel, E., Hugon, J. and Doble, A., *Trends Pharmacol. Sci.*, 1997, 18, 196–203.
Biessels, G. J. and Van Dam, P.S., *Neurosci. Res. Commun.*, 1997, 20, 1–10.
Tomlinson, D.R., Fernyhough, P. and Diemel, L.T., *Diabetes*, 1997, 46 (suppl. 2) S43–S–49.
Hamilton, G.S., *Chem. Ind.*, (London) 1998, 4, 127–132.
Ebadi, M., et al., *Neurochem. Int.*, 1997, 30, 347–374.
Lyons, W. E., et al. (*Proc. Natl. Acad. Sci.*, 1994, 91 (8), 3191–5).
Hoshino, J., Hiraoka, J., Hata, Y., Sawada, S., Yamaoto, Y. *J. Chem. Soc., Perkin Trans.* 1 1995, 6, 693–697.
Moehrle, H., Specks, F. *Arch. Pharm.* (Weinheim, Ger.) 1975, 308, 23–33.
Hawes, E.M., Davis, H.L. *J. Het. Chem.* 1973, 10, 39–42.

* cited by examiner

*Primary Examiner*—Evelyn Mei Huang

(57) ABSTRACT

This invention provides compounds having the following general structure:

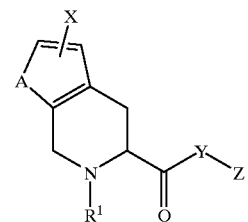

This invention also provides pharmaceutical compositions comprising same and methods of using these compositions to treat and prevent disorders characterized by neuronal damage.

15 Claims, 1 Drawing Sheet

NEUROTROPHIC TETRAHYDROISOQUINOLINES AND TETRAHYDROTHIENOPYRIDINES, AND RELATED COMPOSITIONS AND METHODS

This application claims the benefit of provisional application No. 60/143098, filed Jul. 9, 1999.

FIELD OF THE INVENTION

This invention relates to novel tetrahydroisoquinolines and tetrahydrothienopyridines having neurotrophic activity. These compounds, along with related compositions and methods, are useful in the treatment and prevention of neuronal disorders such as Parkinson's disease, Alzheimer's disease, stroke, multiple sclerosis, amyotrophic lateral sclerosis, diabetic neuropathy and Bell's palsy.

BACKGROUND OF THE INVENTION

Neurodegenerative Diseases

Neurodegenerative diseases constitute a major threat to public health throughout the world. One of the most serious such diseases is Alzheimer's disease ("AD"), a major cause of dementia in aged humans and the fourth most common medical cause of death in the United States. In the U.S., it is estimated that AD afflicts two to three million individuals overall, and more than 5% of the population over the age of 65. Although the exact etiology of AD remains to be defined, the disease is characterized by the presence of a large number of amyloid plaques and neurofibrillary tangles in regions of the brain involved in cognitive function, and degeneration of cholinergic neurons that ascend from the basal forebrain to cortical and hippocampal areas. Currently, there are no effective therapies for AD. Brinton, R. D. and Yamazaki, R. S., *Pharm. Res.*, 1998, 15, 386–398.

Similar to AD, Parkinson's Disease ("PD") is a progressive degenerative disease of the central nervous system ("CNS"). The lifetime incidence of the disease is approximately 2% in the general population. In PD, degeneration of the dopaminergic neurons of the substantia nigra leads to a decrease in dopamine levels in the region of the brain controlling voluntary movement, the corpus striatum. Therefore, standard treatments have focused on the administration of agents, like L-dopa and bromocriptine, which replenish dopamine levels in the affected areas of the brain. Dopaminergic regimens lose their efficacy, however, as nerve cells continue to die and the disease progresses. At the same time the involuntary tremors seen in the early stages of PD advance to periods of difficult movement and, ultimately, to immobility. Therefore, alternative therapies are actively being sought. Pahwa, R. and Koller, W. C., *Drugs Today*, 1998, 34, 95–105.

Neurodegenerative diseases of the somatosensory nervous system also constitute a class of debilitating and potentially lethal conditions. Amyotrophic lateral sclerosis ("ALS") is a fatal disease characterized by progressive degeneration of the upper and lower motor neurons. Although the precise etiology of ALS is unknown, popular theories suggest that excitotoxicity and/or oxidative stress are contributing factors. Riluzole is the first drug approved and marketed for ALS. It possesses antiexcitotoxic properties and has been shown to increase the rate of survival of ALS patients. However, the drug is not a cure, and clinical trials of alternative agents are currently underway. Louvel, E., Hugon, J. and Doble, A., *Trends Pharmacol. Sci.*, 1997, 18, 196–203.

Peripheral neuropathies are secondary to a number of metabolic and vascular conditions. In particular, approximately 30% of patients with diabetes mellitus suffer from some form of peripheral neuropathy that may affect the small myelinated fibers, causing loss of pain and temperature sensation, or the large fibers, causing motor or somatosensory defects. Pharmacotherapeutic intervention tends to be symptomatic, and the best approach to treatment and prevention remains the maintenance of normal blood glucose levels through diet and insulin administration. Biessels, G. J. and Van Dam, P. S., *Neurosci. Res. Commun.*, 1997, 20, 1–10.

A considerable body of evidence now suggests that deficiencies in the levels of certain proteinaceous growth factors, or neurotrophic factors, may play key pathoetiological roles in both peripheral and central neurodegenerative diseases. Tomlinson, D. R., Fernyhough, P. and Diemel, L. T., *Diabetes*, 1997, 46(suppl. 2) S43–S-49; Hamilton, G. S., *Chem. Ind.*, (London) 1998, 4, 127–132; Louvel, E., Hugon, J. and Doble, A., *Trends Pharmacol. Sci.*, 1997, 18, 196–203; Ebadi, M., et al., *Neurochem. Int.*, 1997, 30, 347–374.

These neurotrophic factors can be divided into two structural classes: (1) the neurotrophins, including nerve growth factor ("NGF"), glial cell-derived neurotrophic growth factor ("GDNF"), brain-derived neurotrophic factor ("BDNF"), neurotrophin 3 ("NT-3"), neurotrophin 4/5 ("NT4/5"), and neurotrophin 2 ("NT-2"); and (2) ciliary neurotrophic factor ("CNTF") which is related to the cytokine family of molecules. All neurotrophic factors promote neurite outgrowth, induce differentiation, and suppress programmed cell death or apoptosis in specific subpopulations of peripheral and central neurons. For example, NGF exerts trophic effects on sympathetic and sensory neurons of the dorsal root ganglion and cholinergic neurons of medial septum in the CNS, suggesting potential therapeutic utility in AD. CNTF has trophic actions on a broad cross-section of neurons, including parasympathetic, sensory, sympathetic, motor, cerebellar, hippocampal, and septal neurons. Of particular interest is the fact that CNTF partially prevents the atrophy of skeletal muscle following nerve lesioning but has no effect on innervated muscle, indicating that CNTF is primarily operative in the pathological state. As a result, CNTF is currently being evaluated for its effects in musculoskeletal diseases like ALS.

The clinical utility of proteinaceous neurotrophic agents is severely hampered by their limited bioavailability, especially in the CNS. This necessitates the administration of these agents directly into the brain to induce a therapeutic effect—a relatively hazardous and cumbersome route of administration.

Chemical Agents

Vertex Pharmaceuticals, Inc. (collectively "Vertex") PCT Application WO 96/36630 disclose a series of tetralin compounds that are described as reversing both MPR-mediated and P-glycoprotein-mediated multi-drug resistance, as evidenced by their activity in specific MDR cell lines, and as useful for their ability to maintain, increase, or restore sensitivity of cells to therapeutic or prophylactic agents. The compounds are exemplified by the following structure:

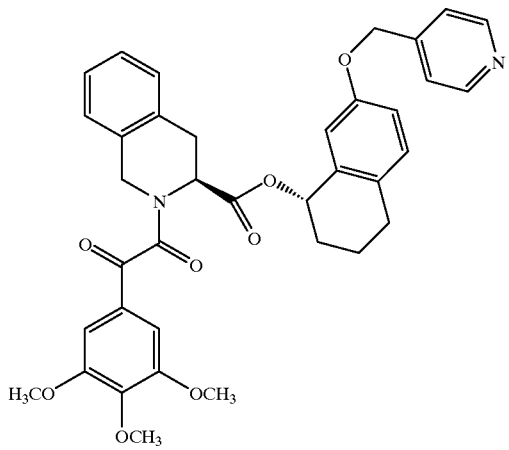

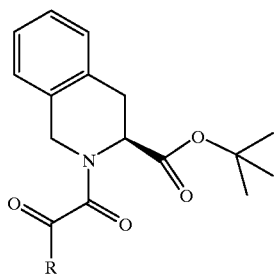

Patents collectively to Syntex (U.S.A.), Inc., (collectively "Syntex") disclose compounds that are described as useful intermediates.

Syntex Application EP 0196841 A1 discloses benzyl N-pyruvoyl-(3)-1,2,3,4-tetrahydroisoquinoline-S-carboxylate compounds that are described as intermediates in the synthesis of a series of N,N-dialkylguanidino dipeptides useful as antihypertensive agents and are typified by the following structure:

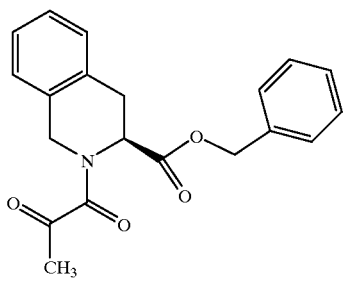

Syntex Application EP 0260118 A1 discloses benzyl N-pyruvoyl-(3)-1,2,3,4-tetrahydroisoquinoline-S-carboxylate compounds that are described as intermediates in the synthesis of ω-guanidino-α-amino acid derivatives and are typified by the following structure:

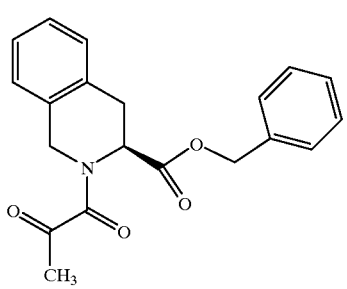

Hoechst Aktiengesellschaft Application EP 0046953 A2 discloses a series of compounds, wherein R is alkyl, aralkyl, heteroarylalkyl, haloalkyl and arylthioalkyl, that are described as intermediates in the synthesis of amino acid analogues with hypotensive activity and are represented by the following structure:

Vertex PCT Application WO 98/20892 discloses methods and compositions containing compounds for stimulating the growth of neurites in nerve cells. The compounds that are described as stimulating neurite outgrowth from pheochromocytoma PC12 cells and are typified by the following structure:

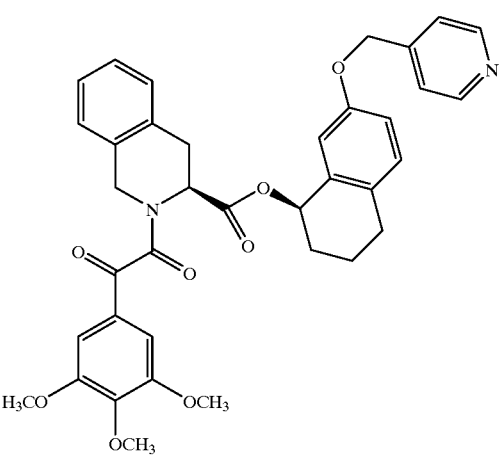

Vertex South African Application 964852 discloses compounds that are described as useful for inhibiting the rotamase activity of the FKBP12 immunophilin and stimulating neurite outgrowth in cell cultures. These compounds are typified by the following structure:

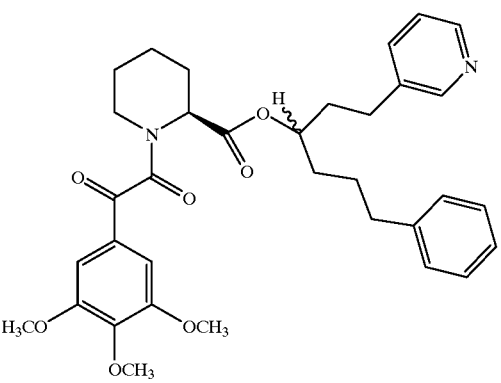

Vertex PCT Application WO 92/19593 discloses a series of compounds that are described as useful for inhibiting the rotamase activity of FK506-binding proteins ("FKBP") and inhibiting T cell activation. These compounds are exemplified by the following structure:

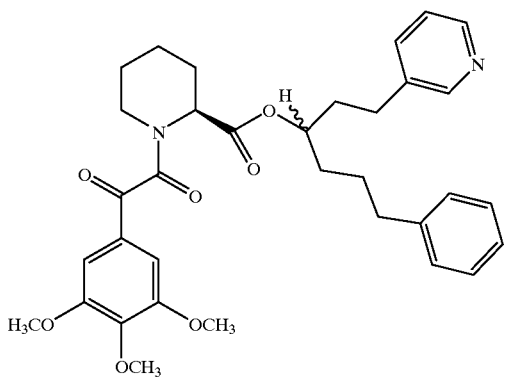

Vertex PCT Application WO 94/07858 discloses a series of compounds that are described as useful multi-drug-resistant cancer cell-sensitizers for maintaining, increasing or restoring the sensitivity of cells to therapeutic or prophylactic agents. The compounds are exemplified by the following structure:

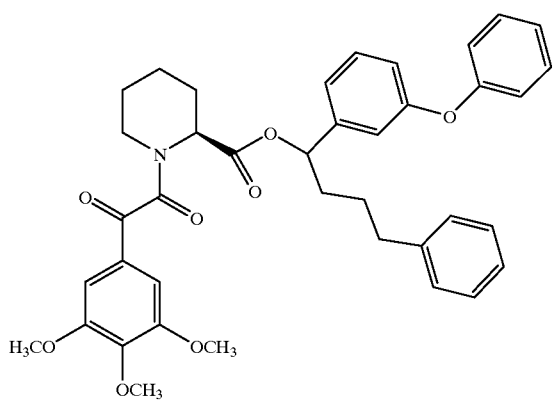

Lyons, W. E., et al. (*Proc. Natl. Acad. Sci.*, 1994, 91(8), 3191–5) describe the neurotrophic effects of the immunosuppressant drug FK506, which shows neurotrophic activity in cultures of PC12 cells and sensory ganglia:

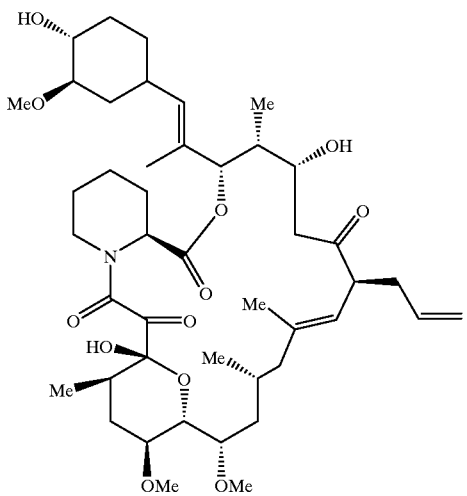

Patents collectively to Guilford Pharmaceuticals, Inc., GPI NIL Holdings, Inc. and Johns Hopkins University School of Medicine (collectively "Guilford") disclose compounds that are described as useful for inhibiting the activity of FKBP-type immunophilins, stimulating neuronal growth and regeneration, and treating neurological disorders.

In particular, Guilford U.S. Pat. No. 5,696,135 and PCT application WO 96/40140 disclose a method of using pipecolic acid derivative compounds, related to FK506 and rapamycin, to treat a neurological disorder in an animal. The compounds therein are described as useful for inhibiting the rotamase activity of an FKBP-type immunophilin, stimulating neuronal growth in chick dorsal root ganglion in vitro, and promoting repair of lesioned sciatic nerves in rats.

Guilford U.S. Pat. No. 5,798,355 discloses a method of using macrocyclic and acyclic pipecolic acid derivatives, which it describes as inhibiting the enzyme activity of FKBP-type immunophilins and stimulating neuronal growth and regeneration.

Guilford U.S. Pat. Nos. 5,614,547 and 5,795,908, and PCT application WO 96/40633, disclose a series of Nglyoxyl-prolyl ester compounds that are described as useful for inhibiting the rotamase activity of the FKBP-12 immunophilin, promoting neuronal growth and regeneration, and treating neurological disorders. The compounds are typified by the following structure:

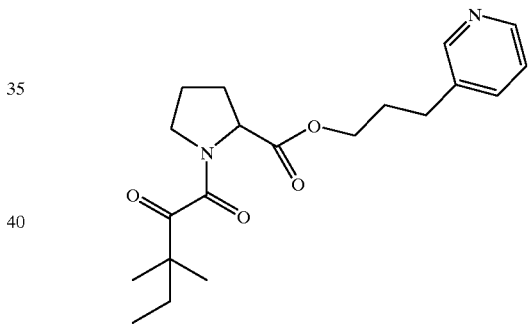

Guilford U.S. Pat. No. 5,801,197 and PCT application WO 97/16190 disclose a series of nonimmunosuppressive pipecolic acid derivatives that are described as useful for the treatment of damaged nerves in animals. The following are representative analogs of the series:

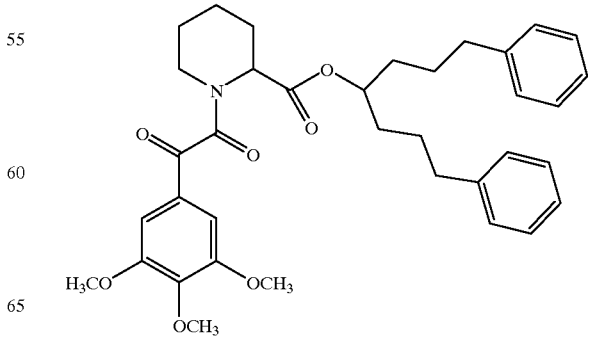

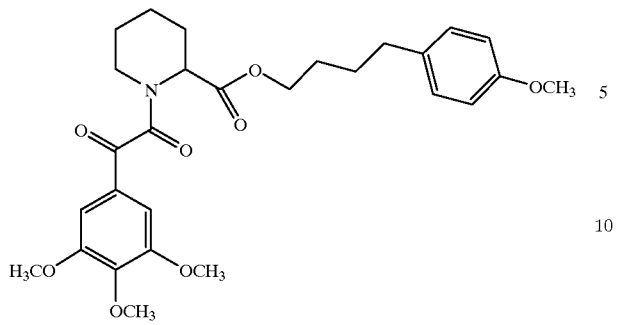

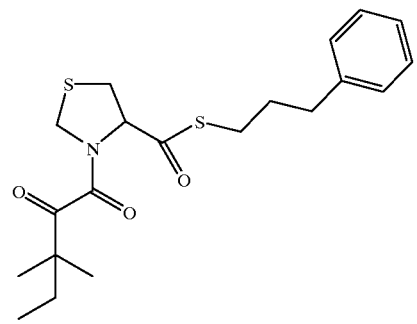

Guilford U.S. Pat. No. 5,721,256 discloses compounds that are described as useful for inhibiting the rotamase activity of FKBP, promoting neuronal growth and regeneration, and effecting neuronal activity in an animal. The series of sulfonamide compounds are typified by the following structure:

Guilford PCT Application WO 98/29116 discloses a series of N-linked sulfonamide compounds of heterocyclic thioesters that are described as useful for inhibiting the rotamase activity of FKBP, promoting neuronal growth and regeneration, and effecting neuronal activity in an animal. The compounds are typified by the following structure:

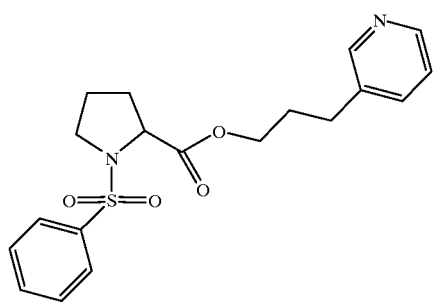

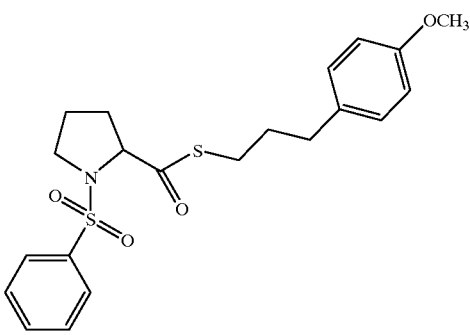

Guilford U.S. Pat. No. 5,801,187 and PCT application WO 98/13355 disclose a series of heterocyclic ester and amide compounds that are described as useful for inhibiting the rotamase activity of FKBP, promoting neuronal growth and regeneration, and effecting neuronal activity in an animal. The compounds are typified by the following structure:

Guilford PCT Application WO 98/29117 discloses a series of N-linked ureas and carbamate compounds of heterocyclic thioesters that are described as useful for inhibiting the rotamase activity of FKBP, promoting neuronal growth and regeneration, and effecting neuronal activity in an animal. The compounds are typified by the following structure:

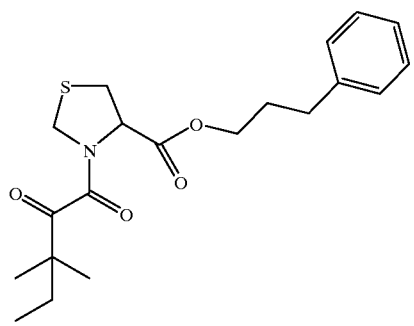

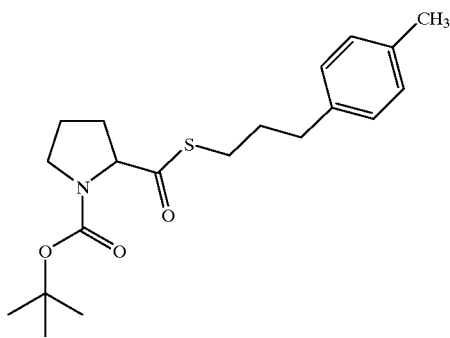

Guilford PCT Application WO 98/13343 discloses a series of heterocyclic thioester and ketone compounds that are described as useful for inhibiting the rotamase activity of FKBP, promoting neuronal growth and regeneration, and effecting neuronal activity in an animal. The compounds are exemplified by the following structure:

Guilford PCT Application WO 98/37882 discloses a method of using small molecule carbamate and urea compounds that are described as useful for inhibiting the rotamase activity of FKBP-type immunophilins and stimulating neuronal growth and regeneration. The compounds are typified by the following structure:

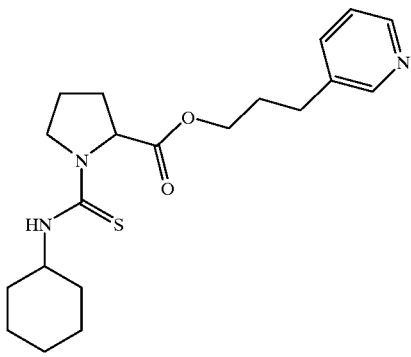

Guilford PCT Application WO 98/37885 discloses a series of Noxide compounds of heterocyclic esters, amides, thioesters and ketones that are described as useful for inhibiting the rotamase activity of FKBP, promoting neuronal growth and regeneration and treating neurological disorders in an animal. The compounds are typified by the following structure:

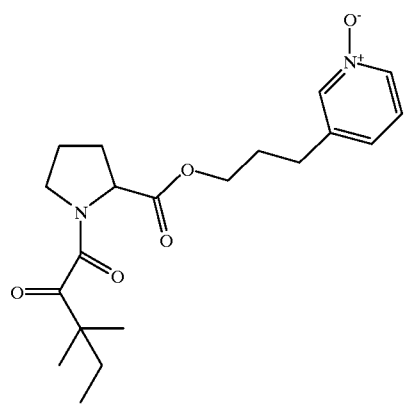

Guilford PCT Application WO 98/25950 discloses a series of tetra- and pentapeptide compounds containing at least two proline residues, which compounds are described as useful for inhibiting the rotamase activity of cyclophilin, promoting neuronal growth and regeneration, and effecting neuronal activity in an animal.

Patents collectively to Cephalon, Inc. and Kyowa Hakko Kogyo Co., Ltd. (collectively "Cephalon") describe small molecule neurotrophic agents with potential clinical utility in the treatment of neurodegenerative diseases.

In particular, Cephalon U.S. Pat. Nos. 5,756,494, 5,621,101 and 5,461,146, and PCT Applications WO 96/13506 and WO 94/02488, disclose a series of indolocarbazole protein kinase inhibitors that are described as having neurotrophic effects in central cholinergic neurons, the dorsal root ganglion and the spinal cord. These compounds are typified by the following structure:

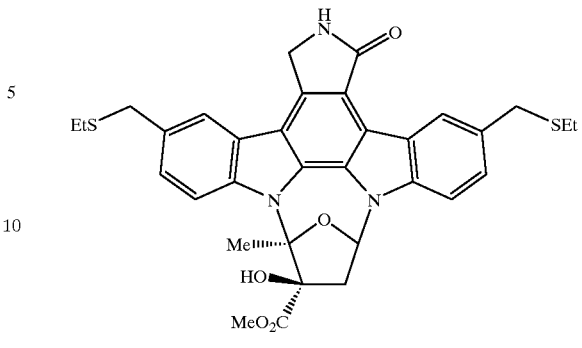

None of the known agents discussed herein has ever been demonstrated as having therapeutic or prophylactic efficacy against neurodegenerative disorders in humans. Thus, there exists a strong and unmet need for agents having such efficacy.

SUMMARY OF THE INVENTION

This invention provides a compound having the structure:

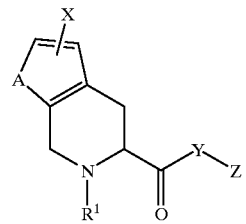

or a pharmaceutically acceptable salt thereof, wherein
(a) $R^1$ is selected from the group consisting of
  (i) $COCOR^2$, wherein $R^2$ is ($C_1$–$C_6$)-straight or branched alkyl, ($C_1$–$C_6$)-straight or branched alkenyl, ($C_5$–$C_7$)-cycloalkyl, 2-thienyl, 3-thienyl, phenyl, or substituted phenyl (the substituted phenyl ring having one to three substituents independently selected from the group consisting of lower alkyl, lower alkoxy, hydroxy and halogen),
  (ii) $CONHR^3$, wherein $R^3$ is ($C_1$–$C_6$)-straight or branched alkyl, and
  (iii) $SO_2R^4$, wherein $R^4$ is phenylalkyl or substituted phenylalkyl (the substituted phenyl ring having one to three substituents independently selected from the group consisting of lower alkyl, lower alkoxy, hydroxy and halogen);
(b) X is selected from the group consisting of hydrogen, lower alkyl, lower alkoxy, hydroxy and halogen;
(c) Y is O or $NR^5$, wherein $R^5$ is ($C_1$–$C_6$)-straight or branched alkyl;
(d) Z is ($C_1$–$C_5$)-straight or branched alkyl or alkenyl substituted in one or more positions with Ar, which Ar is selected from the group consisting of 2-pyridyl, 3-pyridyl, 4-pyridyl, phenyl and substituted phenyl (the substituted phenyl ring having from one to three substituents independently selected from the group consisting of lower alkyl, lower alkoxy, hydroxy and halogen), with the proviso that Z and $R^2$ cannot both be $C_1$-alkyl; and
(e) A is S or CH=CH.

This invention also provides a method of stimulating neuronal growth comprising contacting neurons with an effective amount of the instant compound.

This invention further provides a pharmaceutical composition comprising one of the instant compounds and a pharmaceutically acceptable carrier.

This invention still further provides a method of treating a subject afflicted with a disorder characterized by neuronal damage caused by disease or trauma, comprising administering to the subject a therapeutically effective amount of the instant pharmaceutical composition.

Finally, this invention provides a method of inhibiting in a subject the onset of a disorder characterized by neuronal damage caused by disease, comprising administering to the subject a prophylactically effective amount of the instant pharmaceutical composition.

DETAILED DESCRIPTION OF THE INVENTION

Figure 1:
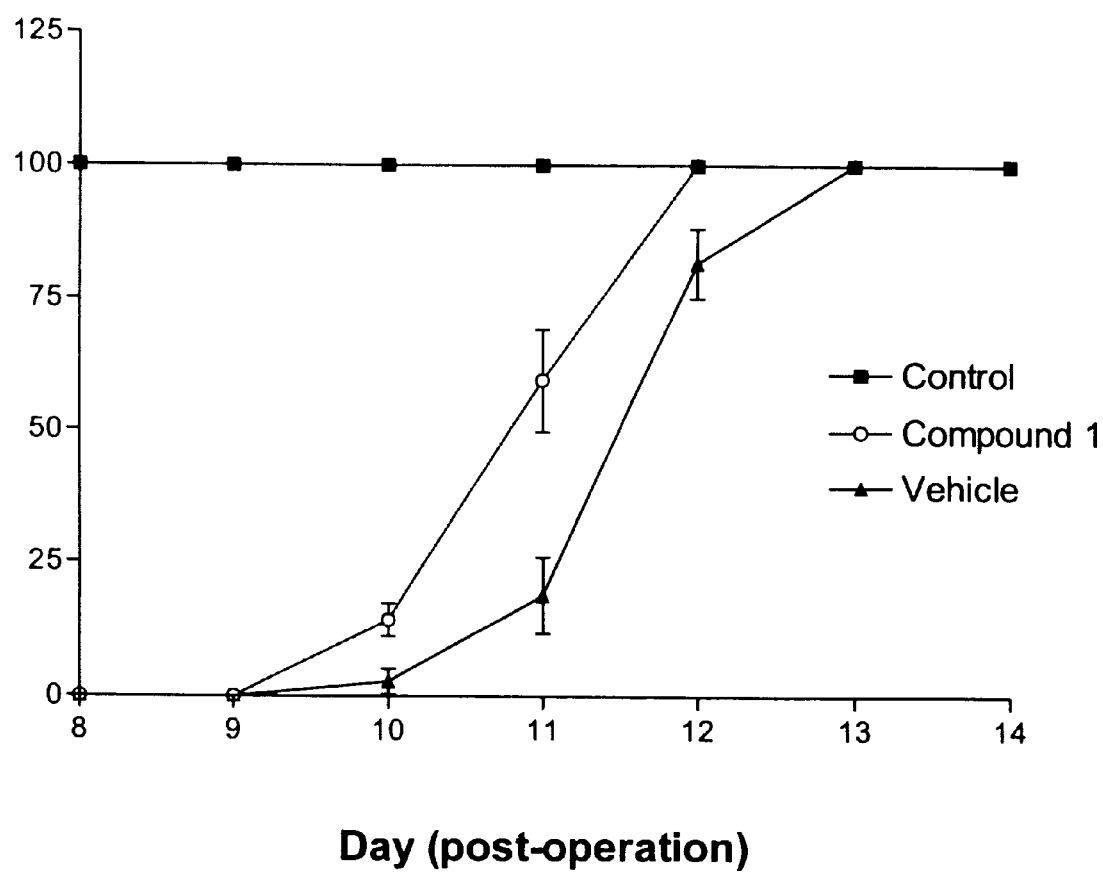
FIG. 1 shows the in vivo biological activity of instant Compound 1 using the rat facial nerve compression model. In this model, compressing the facial nerve causes paralysis of the whisker muscle on that side of the face. The untreated facial nerve on the other side functions as an internal control. Treatment with Compound 1 demonstrated that whisker movement on the paralyzed side was restored more rapidly compared to treatment with a vehicle and the internal control. The whisker movement recovery rate on the paralyzed side compared to the vehicle and internal control is shown in this figure.

This invention provides novel tetrahydroisoquinoline and tetrahydrothienopyridine compounds having surprising neurotrophic activity. These compounds, along with related pharmaceutical compositions and methods, are useful in the treatment and prevention of neuronal disorders such as Parkinson's disease, Alzheimer's disease, stroke, multiple sclerosis, amyotrophic lateral sclerosis, diabetic neuropathy and Bell's palsy, and are useful in the treatment of disorders caused by trauma to the brain, spinal cord or peripheral nerves.

Specifically, this invention provides a compound having the structure:

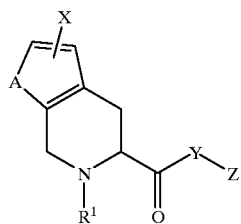

or a pharmaceutically acceptable salt thereof, wherein
(a) $R^1$ is selected from the group consisting of
  (i) $COCOR^2$, wherein $R^2$ is $(C_1-C_6)$-straight or branched alkyl, $(C_{1-C6})$-straight or branched alkenyl, $(C_5-C_7)$-cycloalkyl, 2-thienyl, 3-thienyl, phenyl, or substituted phenyl (the substituted phenyl ring having one to three substituents independently selected from the group consisting of lower alkyl, lower alkoxy, hydroxy and halogen),
  (ii) $CONHR^3$, wherein $R^3$ is $(C_1-C_6)$-straight or branched alkyl, and
  (iii) $SO_2R^4$, wherein $R^4$ is phenylalkyl or substituted phenylalkyl (the substituted phenyl ring having one to three substituents independently selected from the group consisting of lower alkyl, lower alkoxy, hydroxy and halogen);
(b) X is selected from the group consisting of hydrogen, lower alkyl, lower alkoxy, hydroxy and halogen;
(c) Y is O or $NR^5$, wherein $R^5$ is $(C_1-C_6)$-straight or branched alkyl;
(d) Z is $(C_1-C_5)$-straight or branched alkyl or alkenyl substituted in one or more positions with Ar, which Ar is selected from the group consisting of 2-pyridyl, 3-pyridyl, 4-pyridyl, phenyl and substituted phenyl (the substituted phenyl ring having from one to three substituents independently selected from the group consisting of lower alkyl, lower alkoxy, hydroxy and halogen), with the proviso that Z and $R^2$ cannot both be $C_1$-alkyl; and
(e) A is S or CH=CH.

In one embodiment of this compound, Z is $C_3$-straight alkyl substituted in one or more positions with 3-pyridyl. In another embodiment, $R^1$ is $COCOR^2$, $R^2$ being $C_5$-branched alkyl. In an additional embodiment, A is CH=CH. In the preferred embodiment, this compound is selected from the group consisting of instant Compounds 1, 3, 4, 5, 6, 7, 10 and 12.

The instant compounds can be isolated and used as free bases. They can also be isolated and used as pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, palmoic, 2-naphthalenesulfonic, p-toluenesulfonic, cyclohexanesulfamic and saccharic.

This invention also provides a method of stimulating neuronal growth comprising contacting neurons with an effective amount of the instant compound. The contacting can be performed, for example, in vitro, ex vivo or in vivo.

This invention further provides a pharmaceutical composition comprising the instant compound and a pharmaceutically acceptable carrier.

Pharmaceutically acceptable carriers are well known to those skilled in the art and include, but are not limited to, from about 0.01 to about 0.1 M and preferably 0.05 M phosphate buffer or 0.8% saline. Such pharmaceutically acceptable carriers can be aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media. Oral carriers can be elixirs, syrups, capsules, tablets and the like. The typical solid carrier is an inert substance such as lactose, starch, glucose, methyl-cellulose, magnesium stearate, dicalcium phosphate, mannitol and the like. Parenteral carriers include sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject afflicted with a disorder characterized by neuronal damage caused by disease or trauma, comprising administering to the subject a therapeutically effective amount of the instant pharmaceutical composition.

As used herein, the term "subject" includes, without limitation, any animal or artificially modified animal. In the preferred embodiment, the subject is a human.

Administering the instant pharmaceutical composition can be effected or performed using any of the various methods known to those skilled in the art. The instant compounds can be administered, for example, intravenously, intramuscularly, orally and subcutaneously. In the preferred embodiment, the instant pharmaceutical composition is administered orally. Additionally, administration can comprise giving the subject a plurality of dosages over a suitable period of time. Such administration regimens can be determined according to routine methods.

Disorders characterized by neuronal damage are numerous and include the following, without limitation: Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohffart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia).

Other disorders include, without limitation, diffuse white matter disease (Binswanger's disease), head trauma and diffuse brain damage, spinal cord injury, intracranial and intravertebral lesions (including, but not limited to, contusion, penetration, shear, compression and laceration), stroke resulting from cerebral ischemia or infarction, embolic occlusion and thrombotic occlusion, and intracranial hemorrhage of any type (including, but not limited to, epidural, subdural, subarachnoid and intracerebral).

Further disorders include, without limitation, demyelinating diseases such as multiple sclerosis; polyradiculoneuritis (Guillain-Barré syndrome); subacute demyelinating polyneuropathies; brain lesions induced by acute disseminated encephalomyelitis, acute hemorrhagic leukoencephalitis or systemic lupus erythematosus; Behcet's syndrome associated with multifocal brain lesions, neuropathy and/or myelopathy; sarcoidosis associated with nerve damage or atrophy or myelopathy; bacterial or viral infections resulting in brain, spinal cord, nerve damage, meningoradiculitis, and/or myelopathy; subacute combined degeneration; transverse myelitis; Leber's hereditary neuropathy; subacute necrotic encephalopathy (Leigh's disease); mitochondrial encephalopathy with demyelination; metachromatic leukodystrophy; Krabbe's disease; Fabry's disease; adrenoleukodystrophy; neuromyelitis optica (Devic's syndrome); demyelinating Schwannopathies; cranial and peripheral neuropathies including, but not limited to, Déjerine-Sottas neuropathy and its variants; Charcot-Marie-Tooth disease and its variants; hereditary polyneuropathies; sensory and motor neuropathies; axonal neuropathies; adrenomyeloneuropathy; Refsum's disease; neuropathies due to porphyria, acute or chronic toxins/drugs intoxications with either axonal, demyelinating, sensory, motor and/or autonomic involvement; Friedreich's ataxia; ataxiatelangiectasia; and metachromatic leukodystrophy; chronic neuropathies, including, but not limited to, diabetes mellitus and other metabolic dysregulations and dysproteinemias (metabolic neuropathies including those due to alcoholism); and inflammatory/immunological processes (inflammatory neuropathies, herpes zoster-associated neuropathy, and leprous neuritis).

Further disorders include, without limitation, the traumatic neuropathies of the peripheral or cranial nerves, Bell's palsy and other facial nerve neuropathies, trigeminal neuropathy, vestibular neuropathy, accessory nerve neuropathy, vagal neuropathy, glossopharyngeal neuropathy, optic nerve neuropathy, oculomotor nerve neuropathy, multiple cranial nerves palsies, plexopathies, root disorders, idiopathic brachial neuritis, plexitis, multifocal neuropathy, and autonomic nervous system neuropathies.

In one embodiment of this invention, the disorder treated is caused by disease, and is selected from the group consisting of Parkinson's disease, Alzheimer's disease, stroke, multiple sclerosis, amyotrophic lateral sclerosis, diabetic neuropathy and Bell's palsy. In another embodiment, the disorder treated is caused by trauma to the brain, spinal cord or peripheral nerves.

This invention still further provides a method of inhibiting in a subject the onset of a disorder characterized by neuronal damage caused by disease, comprising administering to the subject a prophylactically effective amount of the instant pharmaceutical composition.

In one embodiment, the disorder inhibited is selected from the group consisting of Parkinson's disease, Alzheimers disease, stroke, multiple sclerosis, amyotrophic lateral sclerosis, diabetic neuropathy or Bell's palsy.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to inhibit the onset of a disorder, i.e., eliminate, ameliorate and/or delay the disorder's onset. Methods are known in the art for determining therapeutically and prophylactically effective doses for the instant pharmaceutical composition. The effective dose for administering the pharmaceutical composition to a human, for example, can be determined mathematically from the results of animal studies.

In one embodiment, the therapeutically and/or prophylactically effective dose is a dose sufficient to deliver from about 0.01 mg/kg to about 200 mg/kg of body weight of the instant compound. In another embodiment, the therapeutically and/or prophylactically effective dose is a dose sufficient to deliver from about 0.1 mg/kg to about 50 mg/kg. In the preferred embodiment, the therapeutically and/or prophylactically effective dose is a dose sufficient to deliver from about 1 mg/kg to about 30 mg/kg.

This invention will be better understood by reference to the Experimental Details which follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

I. General Synthetic Methods

Representative compounds of the present invention can be synthesized in accordance with the general synthetic methods described below and illustrated in the following schemes.

Scheme 1

Compound I, of the general formula:

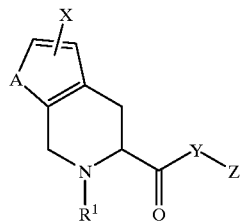
I

[wherein A, X, Y, Z and $R^1$ are as described herein] can be prepared by reaction of Compound II, of the general formula:

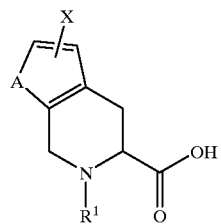
II

[wherein A, X and $R^1$ are as described herein] with an appropriately substituted alcohol or amine in the presence of a coupling agent such as diisopropylcarbodiimide, dicyclohexylcarbodiimide, 1-ethyl-3-(3'-dimethylaminopropyl)carbodiimide hydrochloride (EDCI), benzotriazol-1-yloxytris(dimethylamino)phosphonium hexafluorophosphate (BOP; Castro's reagent), or bromo-tris-pyrrolidinophosphonium hexafluorophosphate (PyBroP) in an inert solvent, such as tetrahydrofuran, dimethylformamide, or methylene chloride at temperatures ranging from about 0° C. to about 37° C. for about 2 to about 48 h (hours).

Frequently, an additive such as hydroxybenzotriazole (HOBt) or 7-azahydroxybenzotriazole (HOAt) is added to suppress racemization during the reaction. Condensations performed with phosphonium (BOP, PyBroP) or uronium salts (HBTU, TBTU, HATU) are conducted with a carboxylate salt as one of the coupling partners. Therefore, an organic amine base, such as diisopropylethylamine, triethylamine or N-methylmorpholine is generally added. Particularly, in the case of condensations performed with a carbodiimide, an acylation catalyst such as camphorsulfonic acid or dimethylaminopyridine may be added.

Scheme 2

Alternatively, Compound I [wherein R' is $COCOR^2$ or $SO_2R^4$ and $R^2$, $R^4$, A, X, Y and Z are as described herein] can be prepared by reaction of Compound III, of the general formula:

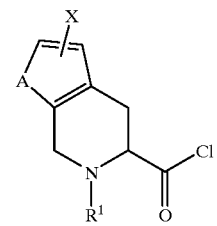
III

[wherein R' is $COCOR^2$ or $SO_2R^4$ and $R^2$, $R^4$, A, and X are as described herein] with an appropriate amine or alcohol in the presence of a organic tertiary amine base, such as diisopropylethylamine, N-methylmorpholine, or triethylamine. The reaction is generally conducted in an inert solvent such as dichloromethane, chloroform, tetrahydrofuran or dioxane, at temperatures ranging from about −20° C. to about 37° C. for about 2 to about 48 h.

Scheme 3

Compound III [wherein R' is $COCOR^2$ or $SO_2R^4$ and $R^2$, $R^4$, A and X are as described herein] can be prepared by reaction of Compound II [wherein R' is $COCOR^2$ or $SO_2R^4$ and $R^2$, $R^4$, A and X are as described herein] with a suitable chlorinating agent such as oxalyl chloride or thionyl chloride, generally in the presence of a catalyst such as dimethylformamide. The reaction is generally conducted in an inert solvent such as dichloromethane, chloroform, tetrahydrofuran, dioxane or benzene at temperatures ranging from about 0° C. to about 80° C. for about 2 to about 24 h.

Scheme 4

Compound II [wherein A, X and $R^1$ are as described herein] can be prepared by reaction of Compound IV, of the general formula:

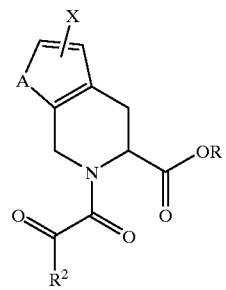
IV

[wherein A, X and $R^1$ are as described herein, and R is lower alkyl] with an alkali metal hydroxide or alkali metal carbonate such as lithium hydroxide, sodium hydroxide or potassium carbonate in a mixed aqueous solvent system such as tetrahydrofuran:water or methanol:water at temperatures ranging from about 0° C. to about 60° C. for about 2 to about 48 h.

Scheme 5

Compound IV [wherein R is lower alkyl and $R^2$, A and X are as described herein] can be prepared by reaction of Compound V, of the general formula:

V

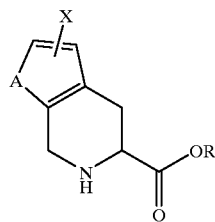

[wherein R is lower alkyl and A and X are as described herein] with a suitably substituted α-ketocarboxylic acid derivative in the presence of a coupling agent such as diisopropylcarbodiimide, dicyclohexylcarbodiimide, 1-ethyl-3-(3'-dimethylaminopropyl)carbodiimide hydrochloride (EDCI), benzotriazol-1-yloxytris(dimethylamino) phosphonium hexafluorophosphate (BOP; Castro's reagent) or bromo-tris-pyrrolidinophosphonium hexafluorophosphate (PyBroP) in an inert solvent such as tetrahydrofuran, dimethylformamide or methylene chloride at temperatures ranging from about 0° C. to about 37° C. for about 2 to about 48 h.

Condensations performed with phosphonium (BOP, PyBroP) or uronium salts (HBTU, TBTU, HATU) are conducted with a carboxylate salt as one of the coupling partners. Therefore, an organic amine base, such as diisopropylethylamine, triethylamine, or N-methylmorpholine is generally added. Particularly in the case of condensations performed with a carbodiimide, an acylation catalyst, such as camphorsulfonic acid or dimethylaminopyridine, also may be added.

Scheme 6

Alternatively, Compound IV [wherein $R^1$ is $COCOR^2$, R is lower alkyl and $R^2$, A and X are as described herein] can be prepared by reaction of Compound VI, of the general formula:

VI

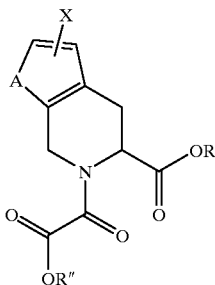

[wherein R and R" are each independently lower alkyl and A and X are as described herein] with a suitably protected Grignard reagent in an inert solvent such as tetrahydrofuran or diethyl ether at temperatures ranging from about −78° C. to about 0° C. for about 2 to about 24 h depending on the reactivity of the oxamate.

Scheme 7

Compound VI, of the general formula:

VII

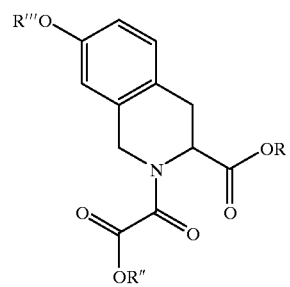

[wherein R, R" and R'" are each independently lower alkyl] can be prepared by reaction of Compound VIII, of the general formula:

VIII

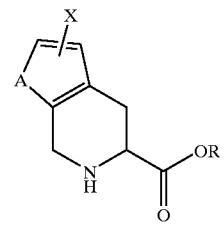

with a lower alkyl halide or sulfonate in the presence of a base such as an alkali metal carbonate, in a suitable organic solvent such as acetone or methyl ethyl ketone. Generally, the reaction is conducted from about room temperature to about 80° C. for about 2 to about 72 h.

Scheme 8

Compound VI [wherein R and R" are each independently lower alkyl and A and X are as described herein] can be prepared by reaction of Compound IX, of the general formula:

IX

[wherein R is lower alkyl and A and X are as described herein] with an alkyl oxalyl chloride in an inert solvent such as methylene chloride for about 2 to about 24 h. Generally, the reaction is conducted in the presence of an organic tertiary amine such as diisopropylethylamine or triethylamine at about 0° C. to about 37° C.

Scheme 9
  Compound X, of the general formula:

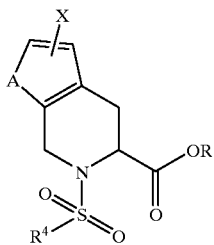

X

[wherein R is lower alkyl and $R_4$, A and X are as described herein] can be prepared by reaction of Compound IX [wherein R is lower alkyl and A and X are as described herein] with a suitably substituted sulfonyl chloride in an inert solvent such as dichloromethane, chloroform, ether, tetrahydrofuran or dioxane in the presence of an organic tertiary amine base such as triethylamine, diisopropylethylamine or N-methylmorpholine. The reaction may be conducted from about 0° C. to about 100° C. for about 2 to about 48 h.
Scheme 10
  Compound XI, of the general formula:

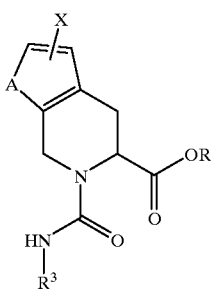

XI

[wherein R is lower alkyl and $R^3$, A and X are as described herein] can be prepared by condensation of Compound IX [wherein R is lower alkyl and A and X are as described herein] with an alkyl isocyanate in an inert solvent such as dichloromethane, chloroform, ether, tetrahydrofuran or dioxane. The reaction may be conducted at temperatures ranging from about 0° C. to about 60° C. for about 2 to about 48 h.
Scheme 11
  Compound IX [wherein R is lower alkyl and A and X are as described herein] can be prepared by reaction of Compound XII, of the general formula:

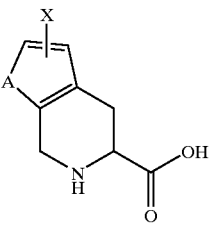

XII

[wherein A and X are as described herein] with a lower alkanol in the presence of an acid catalyst such as hydrogen chloride or p-toluenesulfonic acid. Alternatively, thionyl chloride, sulfuryl chloride or acetyl chloride may be added to the lower alkanol in the presence of Compound XII to effect the desired conversion. The aminoester product is generally isolated as the hydrochloride salt.

When not commercially available, the alcohols and amines used in the synthesis of Compound I, the α-ketocarboxylic acid derivative derivatives and Grgnard reagents used in the synthesis of Compound IV, the sulfonyl chlorides used in the preparation of Compound X, the isocyanates used in the synthesis of Compound XI, the Grignard reagents used in the preparation of Compound IX and the amino acids used in the preparation of Compound VI can be obtained by conventional synthetic procedures, in accordance with literature precedent, from readily accessible starting materials using standard reagents and reaction conditions (see, for example, Hawes, E. M., Davis, H. L. *J. Het. Chem.* 1973, 10, 39–42 and Maffrand, J. P. DE 2800596, published Jul. 13, 1978).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may forn solvates with water (i.e., hydrates) or common organic solvents, and such solvates are also intended to be encompassed within the scope of this invention.

II. Selected Compounds of the Invention

In the preferred embodiment of this invention, the instant compound is selected from the group of compounds shown in Table 1 below.

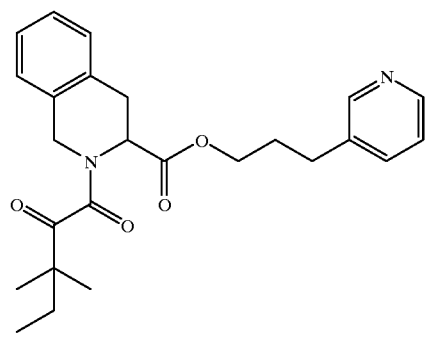

1
Compound 1

-continued
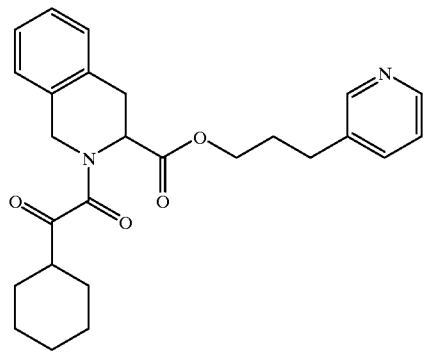
2
Compound 2
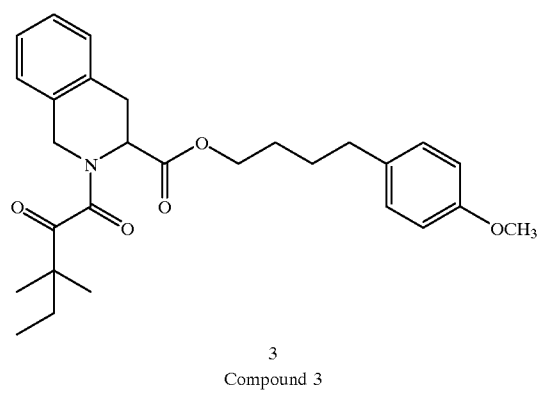
3
Compound 3
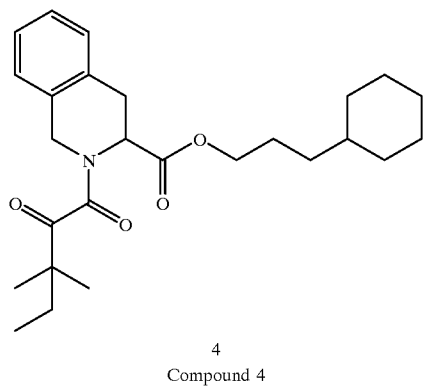
4
Compound 4
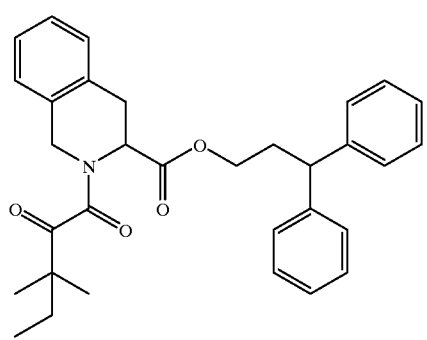
5
Compound 5
-continued
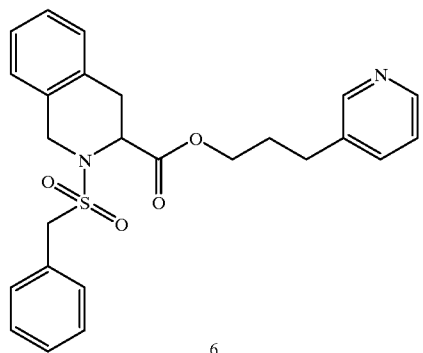
6
Compound 6
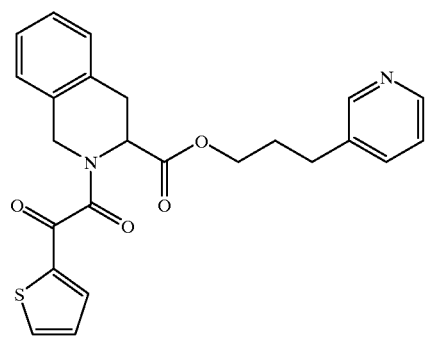
7
Compound 7
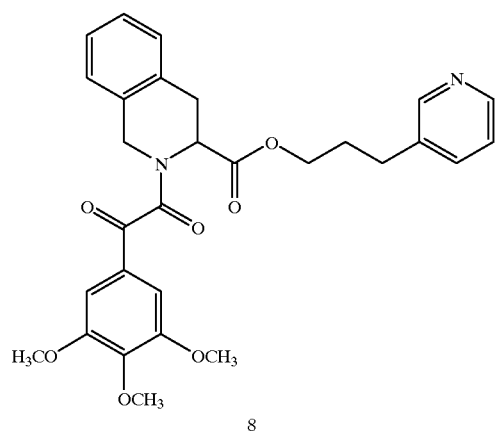
8
Compound 8
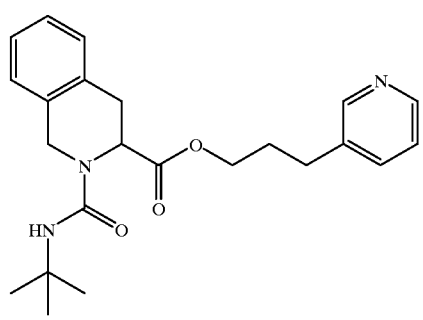
9
Compound 9

-continued

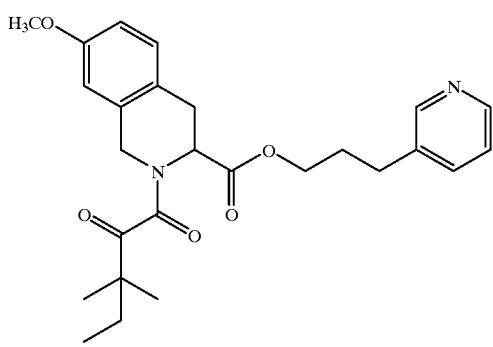

10
Compound 10

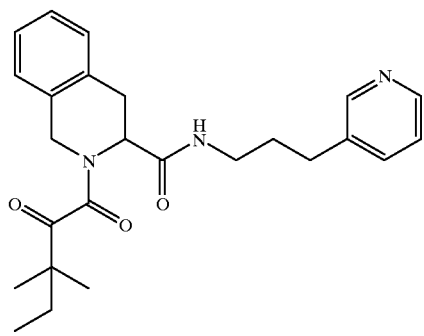

11
Compound 11

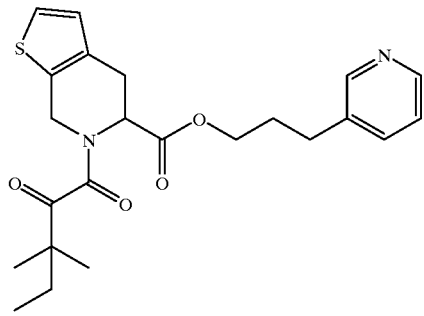

12
Compound 12

III. Specific Synthetic Methods

Specific compounds which are representative of this invention can be prepared as per the following examples. For the sake of clarity, compounds of the invention produced in the following examples are identified by the term "Compound" followed by the appropriate numeral (e.g., "Compound 1"). Intermediates in the synthesis of compounds of the invention are designated as "Reference Examples." No attempt has been made to optimize the yields obtained in these reactions. One skilled in the art would know how to increase such yields through routine variations in reaction times, temperatures, solvents and/or reagents.

The products of some Reference Examples may be used as intermediates to produce more than one of the instant compounds. In those cases, the choice of intermediates to be used to produce subsequent compounds of the present invention is a matter of discretion that is well within the capabilities of those skilled in the art.

REFERENCE EXAMPLE 1

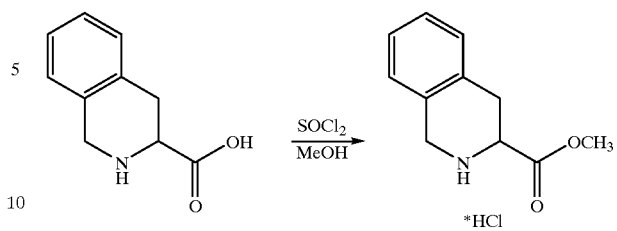

(3S)-Methyl 1,2,3,4-tetrahydro-3-isoquinolinecarboxylate hydrochloride Thionyl chloride (18.7 g, 157.5 mmol) was added dropwise to a solution of (3S)-1,2,3,4-tetrahydro-3-isoquinolinecarboxylic acid (8.0 g, 45 mmol) in methanol (150 mL) at about 0° C. under $N_2$. The solution was warmed to about 25° C., stirred for about 6 h and then concentrated. The residue was washed with ether, followed by 1:1 ether:pentane and dried under vacuum to yield 9.1 g of Reference Example 1 as white solid (89% yield). $^1$H NMR ($d_6$-DMSO): δ 3.27 (m, 2H); 3.82 (s, 3H); 4.35 (s, 2H); 4.59 (m, 1H); 7.28 (s, 4H); 10.35 (br s, 2H).

REFERENCE EXAMPLE 2

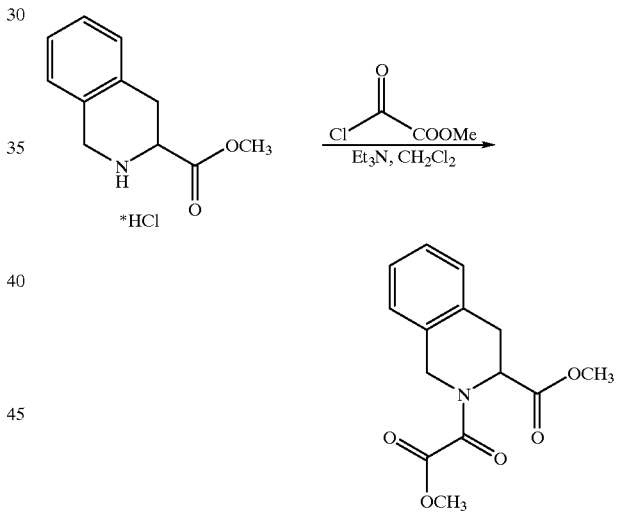

(3S)-Methyl 2-(1,2-dioxo-2-methoxyethyl)-1,2,3,4-tetrahydro-3-isoquinolinecarboxylate To asolution of Reference Compound 1 (8.0 g, 35.1 mmol) in dichloromethane (80 ml) was added triethylamine (7.4 g, 73.7 mmol) dropwise at about 0° C. After stirring for about 15 minutes (min) a solution of methyl oxalyl chloride (6.0 g, 49.1 mmol) in dichloromethane (50 mL) was added. The solution was stirred for about 1.5 h at about 0° C., then was washed with water, dried ($MgSO_4$), and concentrated to yield 9.6 g of Reference Example 2 as a yellow oil (98% yield). $^1$H NMR ($CDCl_3$): δ 3.29 (m, 2H); 3.67 (d, 3H); 3.94 (d, 3H); 4.58–5.00 (m, 2H); 5.06, 5.38 (2 m's, 1H); 7.09–7.28 (m, 4H).

REFERENCE EXAMPLE 3

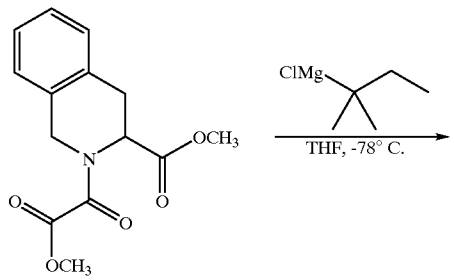

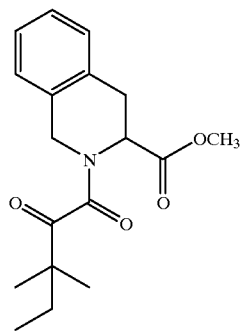

(3S)-Methyl 2-(1,2-dioxo-3,3-dimethylpentyl)-1,2,3,4-tetrahydro-3-isoquinolinecarboxylate To a solution of Reference Example 2 (9.5 g, 34.2 mmol) in THF (100 mL) at −78° C. was added dropwise a solution of dimethylpropyl magnesium chloride in diethyl ether (1M solution, 44.5 mL). The solution was stirred at about −78° C. for about 3 h, then was poured into a solution of saturated ammonium chloride (400 mL), and extracted into ethyl acetate. The organic layers were combined, dried (MgSO$_4$), and concentrated. The resulting residue was purified by silica gel column chromatography, eluting with 3% methanol in methylene chloride, to yield 10.2 g of Reference Example 3 as a yellow oil (93% yield). The NMR spectrum contains a doubling of resonances due to cis-trans amide rotamers. $^1$H NMR (CDCl$_3$): δ 0.85–0.97 (m, 3H); 1.20–1.32 (m, 6H); 1.69–1.84 (m, 2H); 3.16–3.35 (m, 2H); 3.67 (d, 3H); 4.44–5.11 (m, 2H); 4.63, 5.29 (2 m's, 1H); 7.03–7.28 (m, 4H).

REFERENCE EXAMPLE 4

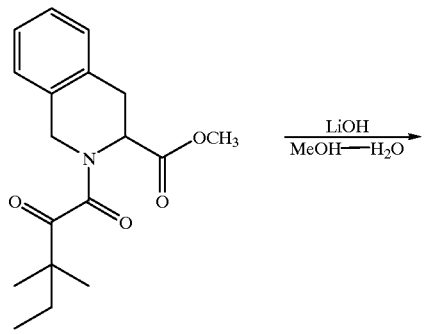

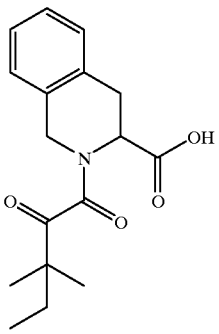

(3S)-2-(1,2-dioxo-3,3-dimethylpentyl)-1,2,3,4-tetrahydro-3-isoquinolinecarboxylic acid Reference Compound 3 (9.5 g, 29.9 mmol) was stirred in methanol (100 mL) and lithium hydroxide solution (1N, 54.3 mL) at about 0° C. for about 30 min. The solution was warmed to about 25° C. and stirred about 20 h. Water (100 mL) was added followed by dropwise addition of 1 N hydrochloric acid until the solution's pH reached about pH 1. The solution was extracted into methylene chloride. The organic layers were combined, dried (MgSO$_4$), and concentrated to yield 8.8 g of Reference Example 4 as a yellow oil (97% yield). The NMR spectrum contains a doubling of resonances due to cis-trans amide rotamers. $^1$H NMR (CDCl$_3$) δ 0.84–0.96 (m, 3H); 1.18–1.29 (m, 6H); 1.67–1.82 (m, 2H); 3.17–3.38 (m, 2H); 4.42–5.10 (m, 2H); 4.63,5.29 (m's, 1H); 7.02–7.14 (m, 4H).

COMPOUND 1

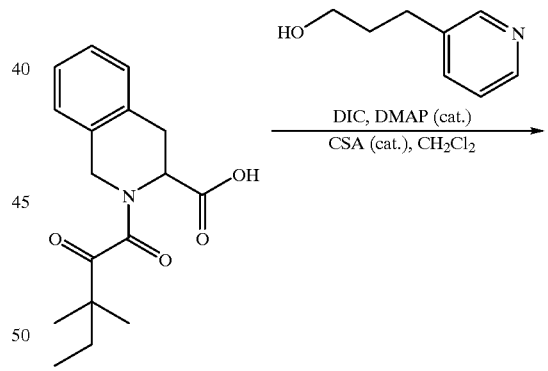

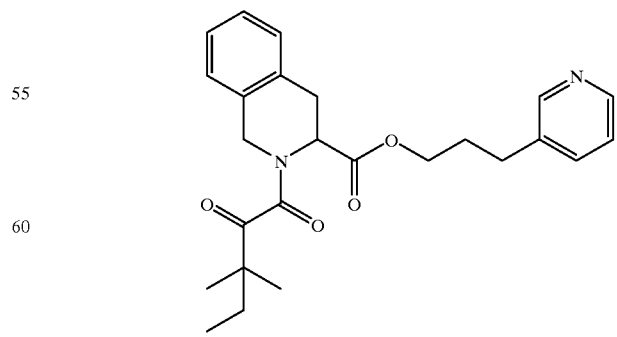

(3S)-3-(3-Pyridyl)-1-propyl 2-(1,2-dioxo-3-dimethylpentyl)-1,2,3,4-tetrahydro-3-isoquinolinecarboxylate To a solution of Reference Example 4 (2.5 g, 8.2 mmol) in methylene chloride (50 mL) was added 4-dimethylaminopyridine (0.30 g, 2.5 mmol), camphorsulfonic acid (0.57 g, 2.5 mmol), diisopropylcarbodiimide (1.66 g, 13.1 mmol), and 3-(3-pyridyl)-1-propanol (1.7 g, 12.3 mmol). The solution was stirred under nitrogen at about 25° C. for about 20 h. The reaction mixture was filtered through Celite and concentrated. The resulting crude residue was purified by silica gel column chromatography, eluting with 3% methanol in methylene chloride, to yield 2.2 g of Compound 1 as yellow oil (63% yield). The NMR spectrum contains a doubling of resonances due to cis-trans amide rotamers. $^1$H NMR (CDCl$_3$): δ 0.86–0.98 (m, 3H); 1.21–1.34 (m, 6H); 1.69–1.92 (m, 2H); 2.47, 2.58 (t's, 2H); 3.18–3.38(m, 2H); 4.12 (m, 4H); 4.46–5.06 (m, 2H); 4.61, 5.31 (m's, 1H); 7.04–7.28 (m, 4H); 7.32–8.49 (series of m's, 4H).

REFERENCE EXAMPLE 5

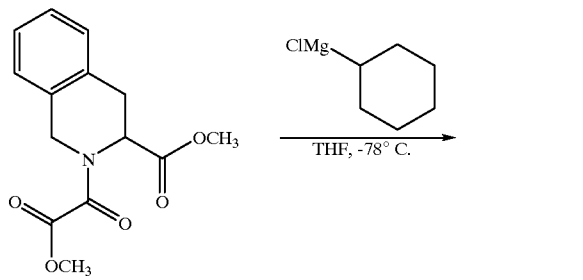

(3S)-Methyl 2-(1,2-dioxo-2-cyclohexylethyl)-1,2,3,4-tetrahydro-3-isoquinolinecarboxylate The title compound was prepared by combining Reference Example 2 (0.5 g, 1.8 mmol) with cyclohexyl magnesium chloride (2M solution, 1.2 mL) in THF (10 mL) following the procedure described for (Reference Example 3). After silica gel column chromatography, eluting with 20% ethyl acetate in pentane, 0.21 g of product was collected as a clear oil (38% yield). The NMR spectrum contains a doubling of resonances due to cis-trans amide rotamers. $^1$H NMR (CDCl$_3$): δ 0.88 (apparent t, 2H); 1.27–1.45 (m, 4H); 1.64–1.98 (m, 5H); 3.17–3.37 (m, 2H); 3.62, 3.69 (s's, 3H); 4.55–5.03 (m, 2H); 4.96, 5.31 (m's, 1H); 7.04–7.24 (m, 4H).

REFERENCE EXAMPLE 6

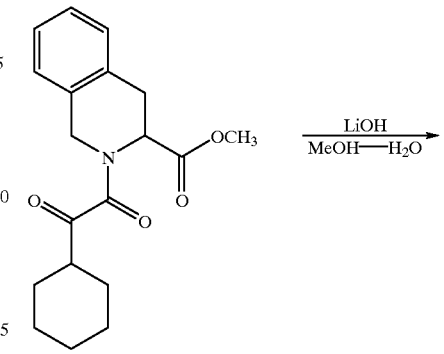

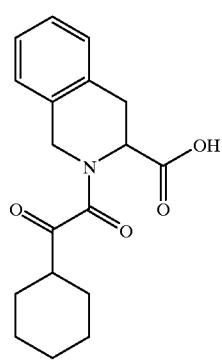

(3S)-2-(1,2-Dioxo-2-cyclohexylethyl)-1,2,3,4-tetrahydro-3-isoquinolinecarboxylic acid The title compound was prepared by stirring Reference Example 5 (0.21 g, 0.64 mmol) in methanol (5 mL) and lithium hydroxide solution (1N, 5 mL), according to the procedure used to synthesize Reference Example 4. The product was collected as a clear oil (0.17 g; 83% yield). The NMR spectrum contains a doubling of resonances due to cis-trans amide rotamers. $^1$H NMR (CDCl$_3$): δ 0.91 (m, 2H); 1.12–1.40 (m, 4H); 1.62–2.08 (m's, 5H); 3.13–3.34 (m, 2H); 4.52–5.00 (m, 2H); 5.27 (m, 1H); 7.01–7.28 (m, 4H).

COMPOUND 2

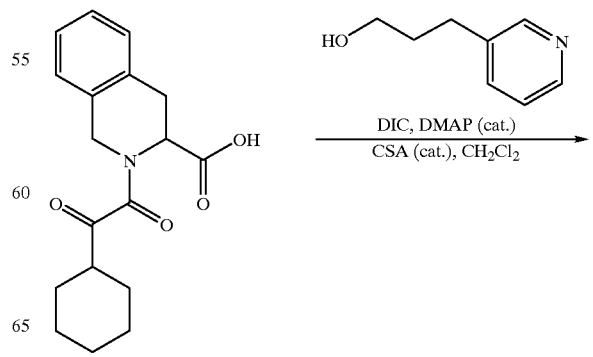

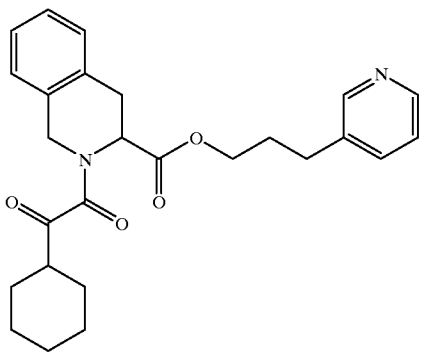

2

(3S)-3-(3-Pyridyl)-1-propyl 2-(1,2-dioxo-2-cyclohexylethyl)-1,2,3,4-tetrahydro-3-isoquinolinecarboxylate The title compound was synthesized following the procedure used for Compound 1. Reference Example 6 (0.166 g, 0.53 mmol) was stirred in methylene chloride (10 mL) with 3-(3-pyridyl)-1-propanol (0.10 g, 0.74 mmol), diisopropylcarbodiimide (0.11 g, 0.85 mmol), 4-dimethylaminopyridine (0.019 g, 0.16 mmol) and camphorsulfonic acid (0.037 g, 0.16 mmol) at about 25° C. for about 20 h. After purification 0.075 g (32% yield) of product was collected as a clear oil. The NMR spectrum contains a doubling of resonances due to cis-trans amide rotamers. $^1$H NMR (CDCl$_3$): δ 0.92 (m, 2H); 1.22–1.42 (m, 4H); 1.65–2.01 (m, 5H); 2.43, 2.55 (t's, 2H); 3.14–3.37 (m, 2H); 4.12 (m, 4H); 4.47–5.00 (m, 2H); 4.98, 5.33 (m's, 1H); 7.09–7.29 (m, 4H); 7.32–8.44 (series of m's, 4H).

COMPOUND 3

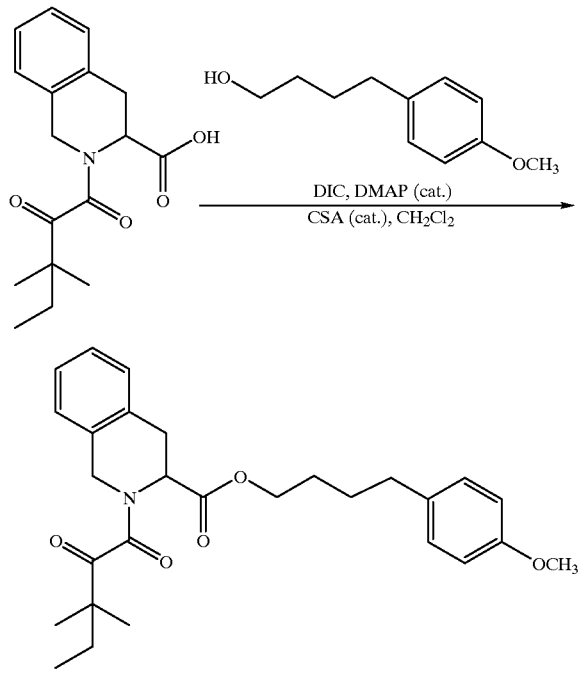

3

(3S)-4-(4-Methoxyphenyl)-1-butyl 2-(1,2-dioxo-3,3-dimethylpentyl)-1,2,3,4-tetrahydro-3-isoquinolinecarboxylate The title compound was synthesized following the procedure for Compound 2. Reference Example 4 (0.5 g, 1.65 mmol) was stirred in methylene chloride (100 mL) with 4-(4-methoxyphenyl)-1-butanol (0.459, 2.5 mmol), dicyclohexylcarbodiimide (0.54 g, 2.6 mmol), 4-dimethylaminopyridine (0.06 g, 0.5 mmol), and camphorsulfonic acid (0.119 g, 0.5 mmol) at about 25° C. for about 20 h. After purification 0.379 of product was collected as a clear oil (48% yield). The NMR spectrum contains a doubling of resonances due to cis-trans amide rotamers. $^1$H NMR (CDCl$_3$): δ 0.87 (m, 3H); 1.25 (overlapping s's, 6H); 1.73 (m, 2H); 2.47 (m, 4H); 2.58 (t, 2H); 3.23 (m, 2H); 3.63, 3.70 (s's, 3H); 4.12 (m, 4H); 4.45–5.01 (m, 2H); 4.61, 5.29 (m's, 1H); 7.01–7.28 (m, 6H); 7.42 (d's, 2H).

COMPOUND 4

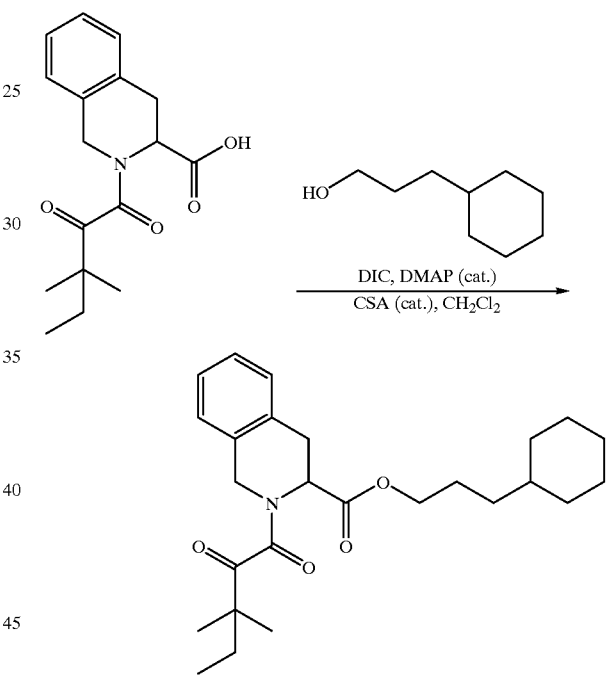

4

(3S)-3-Cyclohexyl-1-propyl 2-(1,2-dioxo-3,3-dimethylpentyl)-1,2,3,4-tetrahydro-3-isoquinolinecarboxylate The title compound was synthesized following the procedure for Compound 2. Reference Example 4 (0.5 g, 1.65 mmol) was stirred in methylene chloride (10 mL) with 3-cyclohexyl-1-propanol (0.36 g, 2.5 mmol), dicyclohexylcarbodiimide (0.54, 2.6 mmol), 4-dimethylaminopyridine (0.06 g, 0.5 mmol), and camphorsulfonic acid (0.11 g, 0.5 mmol) at about 25° C. for about 20 h. After purification 0.16 g of product was collected as a clear oil (21% yield). The NMR spectrum contains a doubling of resonances due to cis-trans amide rotamers. $^1$H NMR (CDCl$_3$): δ 0.90 (m, 5H); 1.12–1.35 (m, 14H); 1.53–1.81 (m, 7H); 3.24 (m, 2H); 3.65 (t, 2H); 4.45–5.09 (m, 2H); 4.62, 5.31 (m's, 1H); 7.03–7.25 (m, 4H).

COMPOUND 5

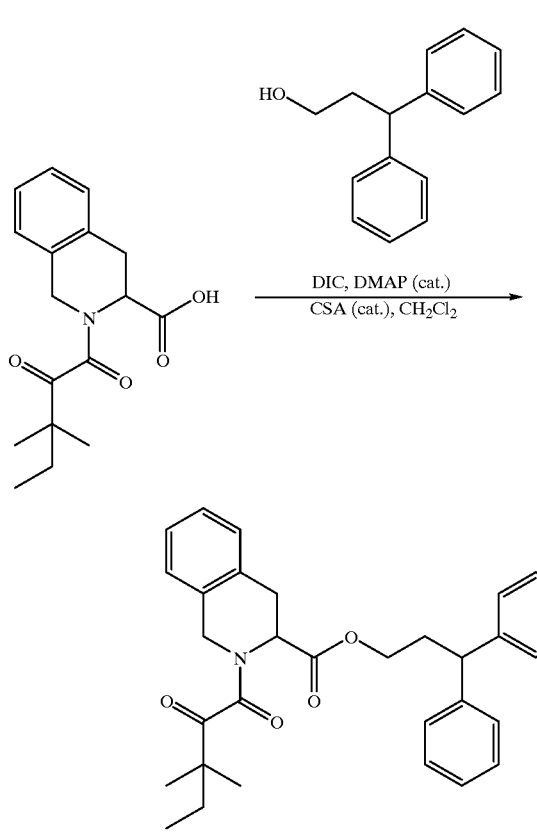

(3S)-3,3-Diphenyl-1-propyl 2-(1,2-dioxo-3,3-dimethylpentyl)-1,2,3,4-tetrahydro-3-isoquinolinecarboxylate The title compound was synthesized following the procedure for Compound 2. Reference Example 4 (0.5 g, 1.65 mmol) was stirred in methylene chloride (10 mL) with 3,3-diphenyl-1-propanol (0.53 g, 2.5 mmol), dicyclohexylcarbodiimide (0.54 g, 2.6 mmol), 4-dimethylaminopyridine (0.06 g, 0.5 mmol), and camphorsulfonic acid (0.11 g, 0.5 mmol) at about 25° C. for about 20 h. After purification 0.37 g (48% yield) of product was obtained as a clear oil. The NMR spectrum contains a doubling of resonances due to cis-trans amide rotamers. $^1$H NMR (CDCl$_3$): δ 0.92 (m, 3H); 1.16–1.38 (m, 6H); 1.68–2.00 (m, 3H); 2.16–2.35 (m, 2H); 3.11 (m, 2H); 4.01 (m, 2H); 4.43–5.06 (m, 2H); 4.74, 5.31 (m's, 1H); 7.01–7.32 (m, 14H).

REFERENCE EXAMPLE 7

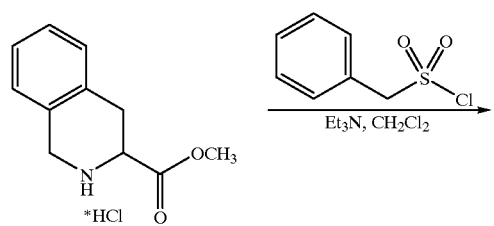

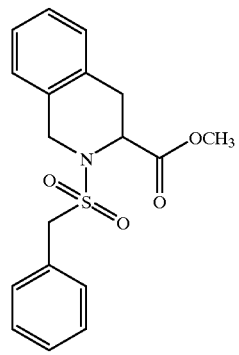

(3S)-Methyl 2-benzylsulfonyl-1,2,3,4-tetrahydro-3-isoquinolinecarboxylate

To a solution of Reference Example 1 (0.5 g, 2.2 mmol) and α-toluenesulfonyl chloride (0.41 g, 2.2 mmol) in dichloromethane (20 mL) was added triethylamine (0.47 g, 4.6 mmol). The solution was stirred for about 20 h at about 25° C., then was filtered through Celite and concentrated. The crude residue was purified by silica gel column chromatography, eluting with 30% ethyl acetate in pentane, to yield 0.26 g of pure product as a clear oil (34% yield). $^1$H NMR (CDCl$_3$): δ 3.11 (m, 2H); 3.68 (s, 3H); 4.37 (ab q, J=5 Hz, 2H); 4.48 (s, 2H); 4.79 (m, 1H); 6.95–7.23 (m, 4H); 7.31–7.43 (m, 5H).

REFERENCE EXAMPLE 8

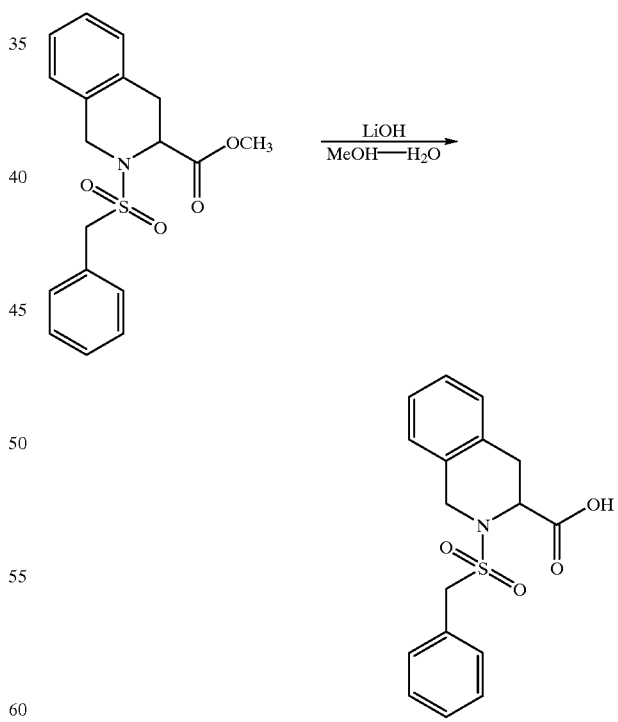

(3S)-2-Benzylsulfonyl-1,2,3,4-tetrahydro-3-isoquinolinecarboxylic acid

Reference Example 7 (0.26 g, 0.75 mmol) was stirred in methanol (5 mL) and lithium hydroxide (1N, 5 mL) overnight at about 25° C. The procedure used to isolate Reference Example 4 was followed to yield 0.23 g of product as a white viscous oil (93% yield). ¹H NMR (CDCl₃): δ 3.06 (m, 2H); 4.35 (m, 2H); 4.48 (s, 2H); 4.74 (m, 1H); 6.96–7.39 (m, 9H).

COMPOUND 6

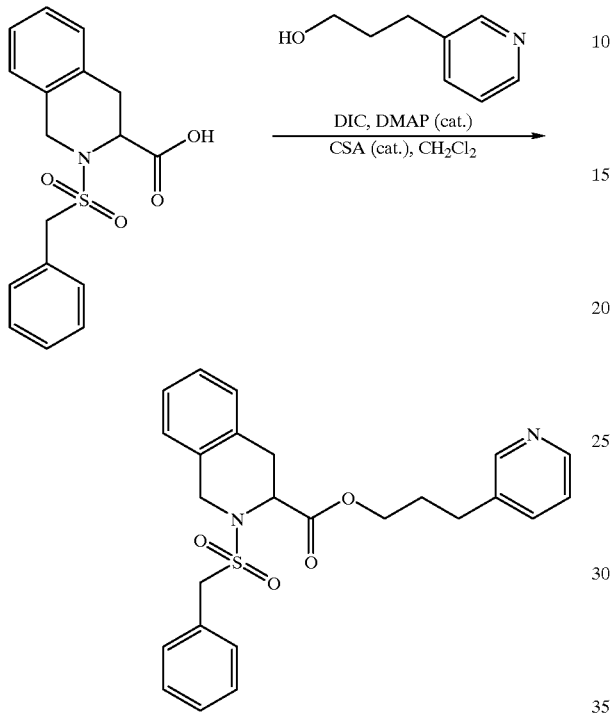

6

(3S)-3-(3-Pyridyl-1-propyl 2-benzylsulfonyl-1,2,3,4-tetrahydro-3-isoquinolinecarboxylate The title compound was prepared according to the procedure used for Compound 1. Reference Example 8 (0.19 g, 0.57 mmol) was stirred in methylene chloride (10 mL) with 3-(3-pyrdyl)-1-propanol (0.11 g, 0.80 mmol), diisopropylcarbodiimide (0.11 g, 0.91 mmol), 4-dimethylaminopyrdine (0.021 g, 0.17 mmol), and camphorsulfonic acid (0.040 g, 0.17 mmol) at about 25° C. for about 20 h. After purification (silica gel chromatography, 3% methanol in methylene chloride eluent) 0.20 g of product was collected as a clear oil (77% yield). ¹H NMR (CDCl₃): δ 1.85 (m, 2H); 2.55 (t, 2H); 3.07 (m, 2H); 4.08 (m, 2H); 4.37 (ab q, J=5 Hz, 2H); 4.50 (s, 2H); 4.72 (m, 1H); 7.03 (m, 1H); 7.16 (m, 4H); 7.38 (m, 6H); 8.39 (m, 2H).

REFERENCE EXAMPLE 9

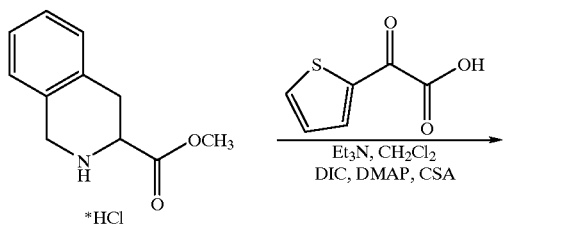

-continued

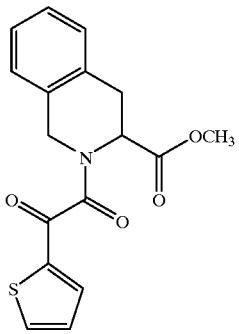

(3S) Methyl 2-(1,2-dioxo-2-(2-thienyl)ethyl)-1,2,3,4-tetrahydro-3-isoquinolinecarboxylate To a solution of Reference Example 1 (0.5 g, 2.2 mmol) in methylene chloride (20 mL) was added triethylamine (0.24 g, 2.4 mmol) dropwise at about 0° C. The solution was stirred for about 30 min at about 0° C., then warmed to about 25° C., after which diisopropylcarbodiimide (0.44 g, 3.5 mmol), 4-dimethylaminopyridine (0.081 g, 0.66 mmol), camphorsulfonic acid (0.15 g, 0.66 mmol), and 2-thiopheneglyoxylic acid (0.52 g, 3.3 mmol) were added. The solution was stirred for about 20 h at about 25° C., then was filtered through Celite and concentrated. The crude residue was purified by silica gel column chromatography, eluting with 20% ethyl acetate in pentane, to yield 0.4 g of product as a yellow oil (54% yield). The NMR spectrum contains a doubling of resonances due to cisrans amide rotamers. ¹H NMR (CDCl₃): δ 3.31 (m, 2H); 3.55, 3.74 (2 s's, 3H); 4.70 (m, 2H); 5.05, 5.43 (2 m's, 1H); 6.98–7.29 (m, 5H); 7.84 (m, 1H); 7.97 (m, 1H).

REFERENCE EXAMPLE 10

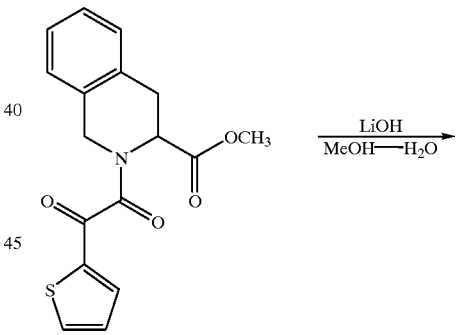

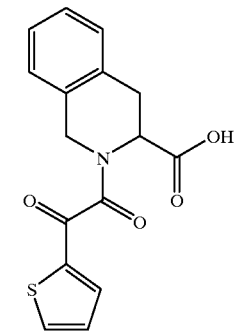

(3S) 2-(1,2-Dioxo-2-(2-thienyl)ethyl)-1,2,3,4-tetrahydro-3-isoquinolinecarboxylic acid A solution of Reference Example 9 (0.14 g, 0.42 mmol) was stirred in methanol (5 mL) and lithium hydroxide solution (1N, 5 mL) overnight at about 25° C. The title compound was isolated according to the procedure used for Reference Example 4 to yield 0.12 g of product as a yellow oil (90% yield). The NMR spectrum contains a doubling of resonances due to cis-trans amide rotamers. $^1$H NMR (CDCl$_3$): δ 3.31 (m, 2H): 4.68 (m, 2H); 5.05, 5.42 (m's, 1H); 7.02 (m, 1H); 7.22 (m, 4H); 7.83 (m, 1H); 7.94 (m, 1H).

COMPOUND 7

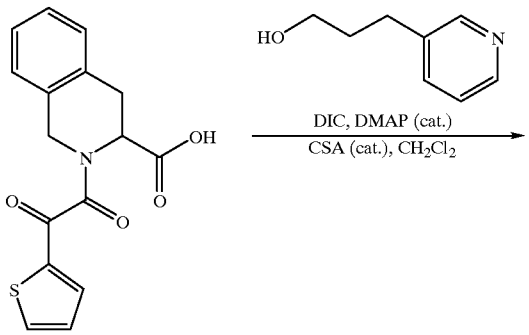

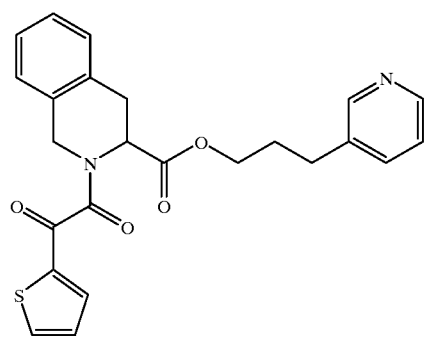

7

(3S) 3-(3-Pyridyl)-1-propyl 2-(1,2-dioxo-2-(2-thienyl)ethyl)-1,2,3,4-tetrahydro-3-isoquinolinecarboxylate The title compound was prepared according to the procedure used for Compound 1. Reference Example 10 (0.13 g, 0.41 mmol) was stirred in methylene chloride (10 mL) with 3-(3-pyridyl)-1-propanol (0.079 g, 0.57 mmol), diisopropylcarbodiimide (0.081 g, 0.66 mmol), and 4-dimethylaminopyridine (0.015 g, 0.12 mmol) at about 25° C. for about 20 h. After purification (silica gel chromatography, 40% ethyl acetate in pentane eluent) 0.052 g of product was collected as a clear oil (29% yield). The NMR spectrum contains a doubling of resonances due to cis-trans amide rotamers. $^1$H NMR (CDCl$_3$): δ 1.74, 1.91 (m's, 2H); 2.20, 2.57 (t's, 2H); 3.33 (m, 2H); 3.98, 4.14 (t's, 2H); 4.72 (m, 2H); 5.06, 5.42 (m's, 1H); 6.99–7.45 (m, 7H); 7.94 (m, 2H); 8.33 (m, 2H).

REFERENCE EXAMPLE 11

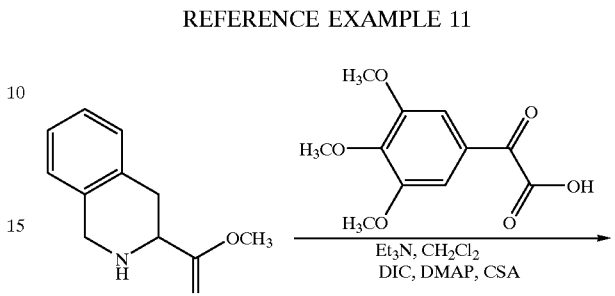

(3S)-Methyl 2-(1,2-dioxo-2-(3,4,5-trimethoxyphenyl)ethyl)-1,2,3,4-tetrahydro-3-isoquinolinecarboxylate The title compound was prepared according to the procedure for Reference Example 9. To a solution of Reference Example 1 (0.59 g, 2.2 mmol) in methylene chloride (20 mL) was added triethylamine (0.24 g, 2.4 mmol) at about 0° C., followed by diisopropylcarbodiimide (0.44 g, 3.5 mmol), 4-dimethylaminopyridine (0.0819 g, 0.66 mmol), camphorsulfonic acid (0.153 g, 0.66 mmol), and 3,4,5-trimethoxyphenylglyoxylic acid (0.75 g, 3.3 mmol) at about 25° C. After purification by silica gel column chromatography, eluting with 40% ethyl acetate in pentane, 0.20 g of product was collected as yellow oil (23% yield). The NMR spectrum contains a doubling of resonances due to cis-trans amide rotamers. $^1$H NMR (CDCl$_3$): δ 3.32 (m, 2H); 3.55, 3.73 (2 s's, 3H); 3.96 (series of overlapping s's, 9H); 4.78 (s, 2H); 4.94, 5.22 (m's, 1H); 6.98 (m, 1H); 7.21 (m, 3H); 7.41 (s, 2H).

REFERENCE EXAMPLE 12

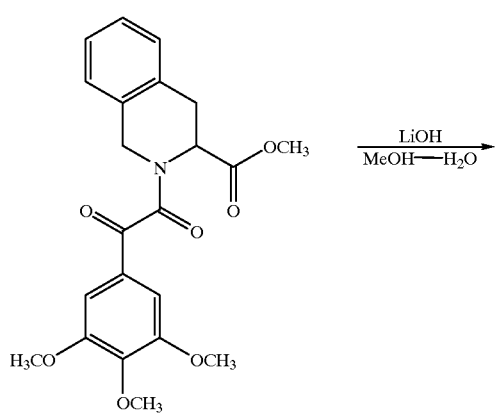

(3S)-2-(1,2-Dioxo-2-(3,4,5-trimethoxyphenyl)ethyl)-1,2,3,4-tetrahydro-3-isoquinolinecarboxylic acid A solution of Reference Example 11 (0.19 g, 0.46 mmol) was stirred in methanol (5 mL) and lithium hydroxide solution (1N, 5 mL) overnight at about 25° C. The title compound was isolated according to the procedure used for Reference Example 4 to yield 0.17 g of product as a yellow oil (91% yield). The NMR spectrum contains a doubling of resonances due to cis-trans amide rotamers. $^1$H NMR (CDCl$_3$) δ 3.35 (m, 2H); 3.91 (overlapping s's, 9H); 4.51–5.20 (m, 2H); 4.77, 5.43 (m's, 1H); 6.98 (m, 1H); 7.22 (m, 3H); 7.36 (s, 2H).

COMPOUND 8

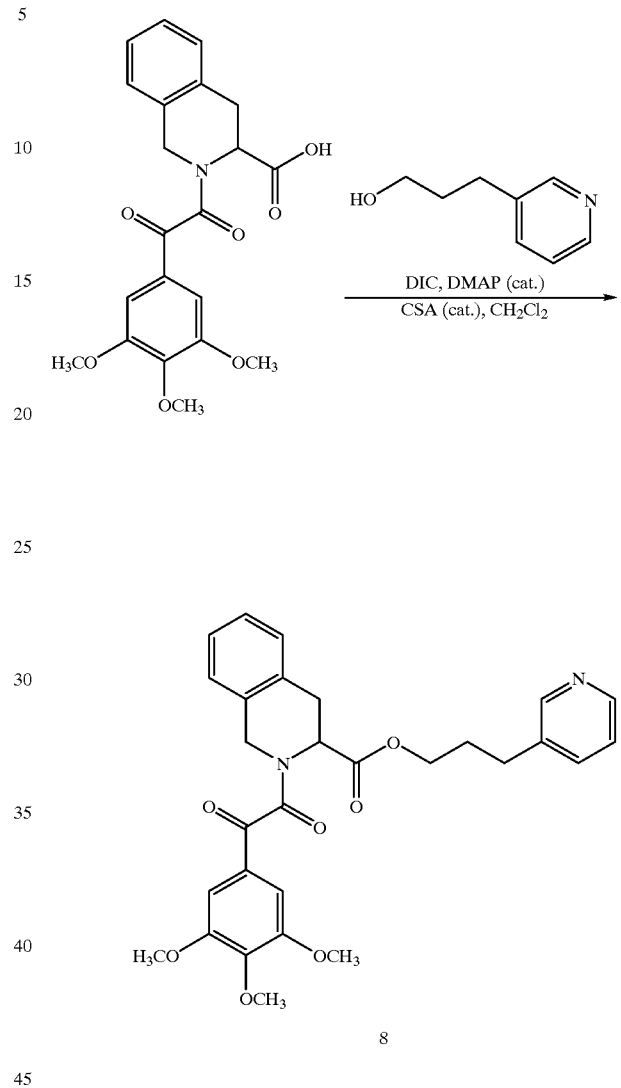

(3S)-3-(3-Pyridyl)-1-propyl 2-(1,2-dioxo-2-(3,4,5-trimethoxyphenyl)ethyl)-1,2,3,4-tetrahydro-3-isoquinolinecarboxylate The title compound was prepared according to the procedure used for Compound 1. Reference Example 12 (0.13 g, 0.41 mmol) was stirred in methylene chloride (10 mL) with 3-(3-pyridyl1-propanol (0.079 g, 0.57 mmol), diisopropylcarbodiimide (0.081 g, 0.66 mmol) and 4-dimethylaminopyridine (0.015 g, 0.12 mmol) at about 25° C. for about 20 h. After purification (silica gel chromatography, 40% ethyl acetate in pentane eluent) 0.052 g of product was collected as a clear oil (29% yield). The NMR spectrum contains a doubling of resonances due to cis-trans amide rotamers. $^1$H NMR (CDCl$_3$) δ 1.71, 1.92 (m's, 2H); 2.38, 2.59 (t's, 2H); 3.33 (m, 2H); 3.93 (series of overlapping s's, 9H); 4.56–5.17 (m, 2H); 4.75, 5.43 (m's, 1H); 6.98 (m, 1H); 7.18 (m, 4H); 7.41 (s, 2H); 8.24–8.48 (series of m's, 2H).

REFERENCE EXAMPLE 13

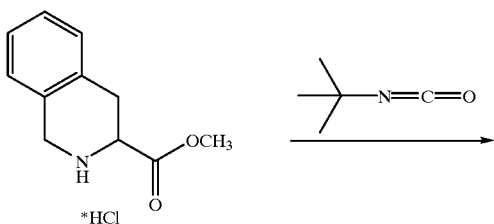

(3S)-Methyl 2-(N-t-butylcarbamoyl)-1,2,3,4-tetrahydro-3-isoquinolinecarboxylate To a solution of Reference Example 1 (0.5 g, 2.2 mmol) in dichloromethane (20 mL) was added dropwise triethylamine (0.47 g, 4.6 mmol). After stirring for about 30 min at about 0° C., t-butyl isocyanate (0.33 g, 3.3 mmol) was added dropwise and the solution was stirred for about 20 h at about 25° C. The solution was filtered through Celite and concentrated. The crude residue was purified by silica gel column chromatography, eluting with 20% ethyl acetate in pentane, to yield 0.33 g of pure product as a clear oil (50% yield). $^1$H NMR (CDCl$_3$) δ 1.41 (s, 9H); 3.22 (m, 2H); 3.58 (s, 3H); 4.50 (m, 2H); 5.37 (m, 1H); 7.15 (m, 4H).

REFERENCE EXAMPLE 14

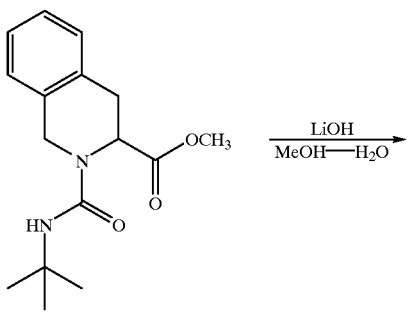

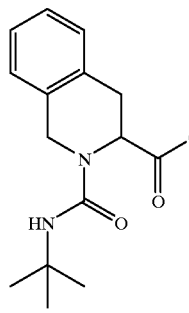

(3S)-2-(N-t-butylcarbamoyl)-1,2,3,4-tetrahydro-3-isoquinolinecarboxylic acid Reference Example 13 (0.33 g, 1.1 mmol) was stirred in methanol (5 mL) and lithium hydroxide (1N, 5 mL) overnight at about 25° C. The procedure used to isolate Reference Example 4 was followed to yield 0.265 g of product as an opaque oil (87% yield). $^1$H NMR (CDCl$_3$) δ 1.43 (s, 9H); 3.29 (m, 2H); 4.36 (m, 2H); 5.01 (m, 1H); 7.22 (m, 4H).

COMPOUND 9

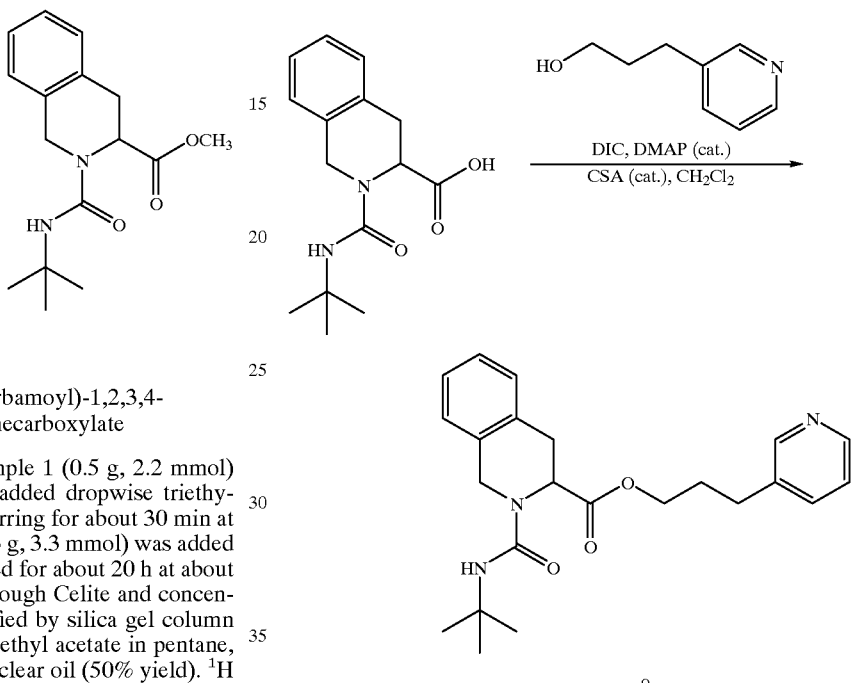

(3S) 3-(3-Pyridyl)-1-propyl 2-(N-t-butylcarbamoyl)-1,2,3,4-tetrahydro-3-isoquinolinecarboxylate The title compound was prepared according to the procedure used for Compound 1. Reference Example 14 (0.215 g, 0.78 mmol) was stirred in methylene chloride (10 mL) with 3-(3-pyridyl)-1-propanol (0.15 g, 1.1 mmol), diisopropylcarbodiimide (0.15 g, 1.2 mmol), 4-dimethylaminopyridine (0.029 g, 0.23 mmol), and camphorsulfonic acid (0.054 g, 0.23 mmol) at about 25° C. for about 20 h. After purification (silica gel chromatography, 5% methanol in methylene chloride eluent) 0.052 g of product was collected as an opaque oil (17% yield). $^1$H NMR (CDCl$_3$) δ 1.43 (s, 9); 1.79 (m, 2H); 2.48 (t, 2H); 3.23 (m, 2H); 3.99 (m, 2H); 4.52 (m, 2H); 5.38 (m, 1H); 7.17 (m, 5H); 7.32 (m, 1H); 8.37 (m, 2H).

REFERENCE EXAMPLE 15

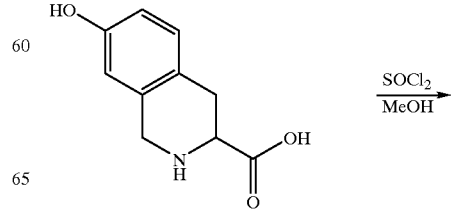

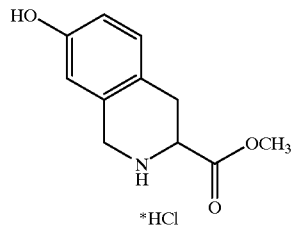

(3S)-Methyl 7-hydroxy-1,2,3,4-tetrahydro-3-isoquinolinecarboxylate hydrochloride Thionyl chloride (1.629, 13.6 mmol) was added dropwise to a solution of (3S)-7-hydroxy-1,2,3,4-tetrahydro-3-isoquinolinecarboxylic acid (0.75 g, 3.9 mmol) in methanol (30 mL) at about 0° C. under $N_2$. The solution was warmed to about 25° C. and stirred for about 6 h, then was concentrated. The residue was washed with ether, followed by 1:1 ether pentane and dried under vacuum to yield 0.85 g of product as a white solid (89% yield). $^1$H NMR ($d_6$DMSO) δ 3.09 (m, 2H); 3.78 (s, 3H); 4.23 (apparent s, 2H); 4.51 (m, 1H); 6.61 (s, 1H); 6.72 (d, J=3 Hz, 1H); 7.04 (d, J=3 Hz, 1H).

REFERENCE EXAMPLE 16

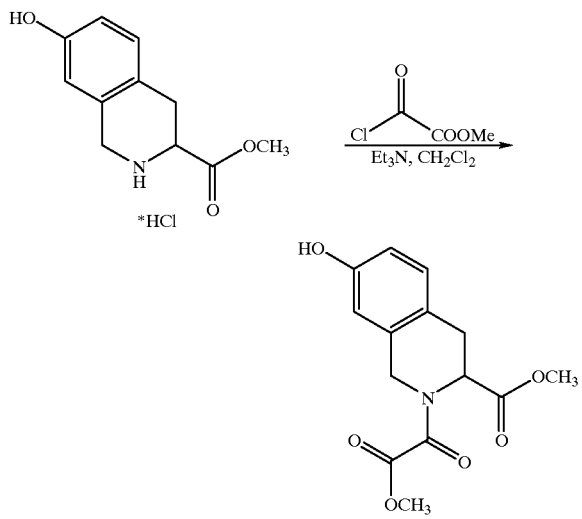

(3S)-Methyl 2-(1,2-dioxo-2-methoxy)ethyl-(7-hydroxy)-1,2,3,4-tetrahydro-3-isoquinolinecarboxylate To a solution of Reference Example 15 (0.4 g, 1.6 mmol) in methylene chloride (15 mL) at about 0° C. was added dropwise diisopropylethylamine (0.21 g, 1.6 mmol) followed by N-methylmorpholine (0.18 g, 1.8 mmol). After stirring for about 30 min at about 0° C., methyl oxalyl chloride (0.28 g, 2.3 mmol) in methylene chloride (2 mL) was added dropwise. The solution was warmed to about 25° C. and stirred for about 1.5 h. The solution was diluted with water and extracted into ethyl acetate. The organic layers were combined, dried ($MgSO_4$), and concentrated. The crude residue was purified by silica gel chromatography, eluting with 3% methanol in methylene chloride, to yield 0.31 g of product as a yellow oil (64% yield). The NMR spectrum contains a doubling of resonances due to cis-trans amide rotamers. $^1$H NMR ($CDCl_3$) δ 3.25 (m, 2H); 3.67 (overlapping s's, 3H); 3.92 (overlapping s's, 3H); 4.76 (overlapping m's, 2H); 5.08, 5.42 (m's, 1H); 6.97–7.24 (overlapping m's, 3H).

REFERENCE EXAMPLE 17

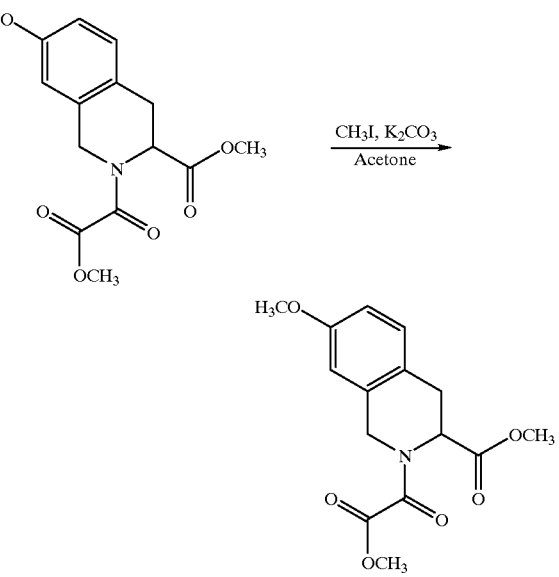

(3S)-Methyl 2-(1,2-dioxo-2-methoxyethyl)-(7-methoxy)-1,2,3,4-tetrahydro-3-isoquinolinecarboxylate To a solution of Reference Example 16 (0.36 g, 1.2 mmol) in acetone (5 mL) was added potassium carbonate (0.17 g, 1.2 mmol) and methyl iodide (0.85 g, 6.0 mmol). The solution was heated to reflux temperature for about 2 h, then cooled and stirred about 20 h at about 25° C. The solution was diluted with water and extracted into ethyl acetate. The organic extracts were combined, dried ($MgSO_4$), and concentrated. The crude residue was purified by silica gel chromatography, eluting with 3% methanol in methylene chloride, to yield 0.33 g of product as a yellow oil (91% yield). The NMR spectrum contains a doubling of resonances due to cis-trans amide rotamers. $^1$H NMR ($CDCl_3$) δ 3.19 (m, 2H); 3.63, 3.68 (s's, 3H); 3.80 (s, 3H); 3.90, 3.97 (2 s's, 3H); 4.54–4.95 (series of m's, 2H); 5.00, 5.36 (m's, 1H); 6.58–7.12 (series of m's, 3H).

REFERENCE EXAMPLE 18

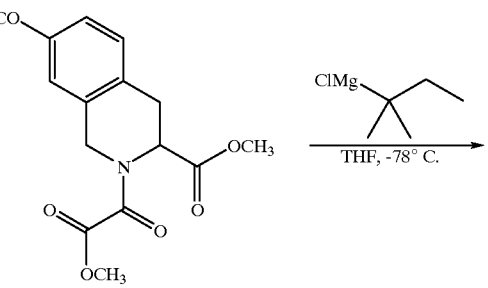

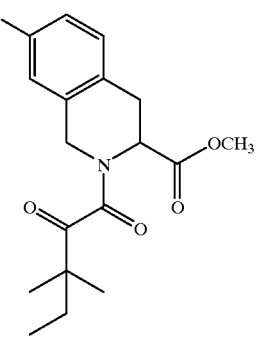

(3S)-Methyl-2-(1,2-dioxo-3-dimethylpentyl)-7-methoxy-1,2,3,4-tetrahydro-3-isoquinolinecarboxylate The title compound was prepared by combining Reference Example 17 (0.334 g, 1.1 mmol) with 1,1-dimethylpropyl magnesium chloride (2M solution, 1.4 mL) in THF (10 mL) following the procedure described for Reference Example 3. After purification (silica gel chromatography, 20% ethyl acetate in pentane eluent), 0.16 g of product was collected as a yellow oil (41% yield). The NMR spectrum contains a doubling of resonances due to cis-trans amide rotamers. $^1$H NMR (CDCl$_3$) δ 0.92 (m, 3H); 1.25 (overlapping s's, 6H); 1.76 (m, 2H); 3.18 (m, 2H); 3.64, 3.69 (s's, 3H); 3.78 (apparent s, 3H); 4.42–5.06 (overlapping m's, 2H); 4.59, 5.28 (m's, 1H); 6.57–7.11 (overlapping m's, 3H).

REFERENCE EXAMPLE 19

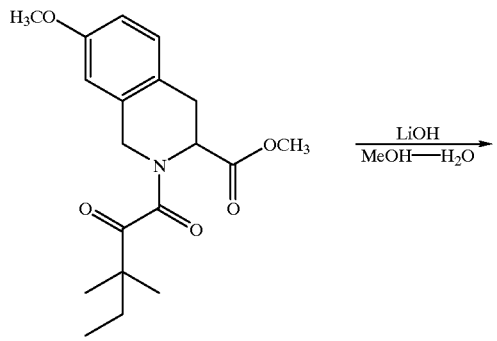

(3S) 2-(1,2-Dioxo-3-dimethylpentyl)-7-methoxy-1,2,3,4-tetrahydro-3-isoquinolinecarboxylic acid Reference Example 18 (0.15 g, 0.45 mmol) was stirred in methanol (5 mL) and lithium hydroxide solution (1N, 5 mL) at about 25° C. for about 20 h. Work-up according to the procedure described for Reference Example 4 afforded 0.14 g of product as a clear oil (98% yield). The NMR spectrum contains a doubling of resonances due to cis-trans amide rotamers. $^1$H NMR (CDCl$_3$) δ 0.92 (m, 3H); 1.26 (overlapping s's, 6H); 1.77 (m, 2H); 3.20 (m, 2H); 3.78 (apparent s, 3H); 4.41–5.06 (overlapping m's, 2H); 4.62, 5.30 (m's, 1H); 6.57–7.14 (overlapping m's, 3H).

COMPOUND 10

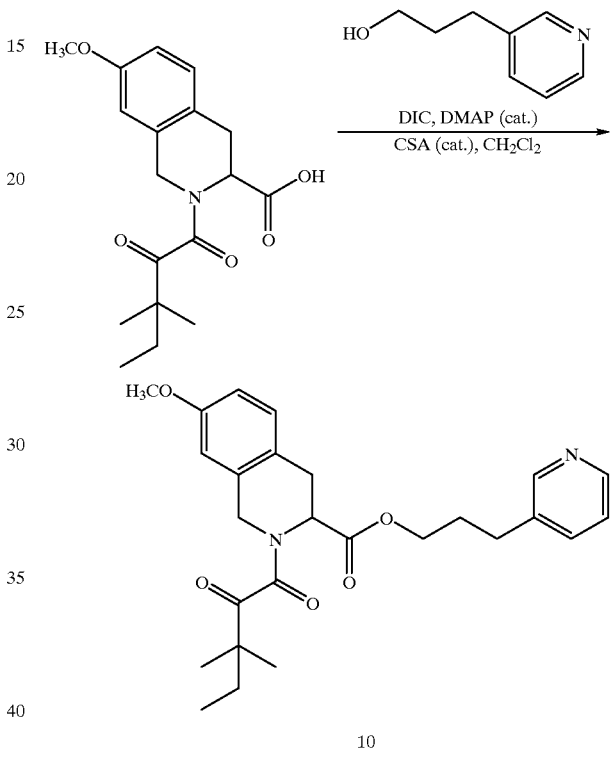

(3S)-3-(3-Pyridyl)-1-propyl 2-(1,2-dioxo-3-dimethylpentyl)-7-methoxy-1,2,3,4-tetrahydro-3-isoquinolinecarboxylate A solution of Reference Example 19 (0.15 g, 0.44 mmol) in methylene chloride (10 mL) with diisopropylcarbodiimide (0.089 g, 0.7 mmol), 4-dimethylaminopyridine (0.016 g, 0.13 mmol), camphorsulfonic acid (0.031 g, 0.13 mmol) and 3-(3-pyridyl)-1-propanol (0.085 g, 0.67 mmol) was stirred at about 25° C. for about 20 h. Following work-up according to the procedure used for Compound 1 and purification by silica gel chromatography (40% ethyl acetate in pentane), 0.051 g of product was collected as a clear oil (26% yield). The NMR spectrum contains a doubling of resonances due to cis-trans amide rotamers. $^1$H NMR (CDCl$_3$) δ 0.91 (m, 3H); 1.25 (overlapping s's, 6H); 1.81 (overlapping m's, 4H); 2.47, 2.55 (t's, 2H); 3.28 (m, 2H); 3.73 (apparent s, 3H); 4.07 (m, 2H); 4.42–5.03 (overlapping m's, 2H); 4.59, 5.29 (m's, 1H); 6.59–7.24 (overlapping m's, 4H); 7.38 (m, 1H); 8.35 (m, 1H); 8.43 (m, 1H).

COMPOUND 11

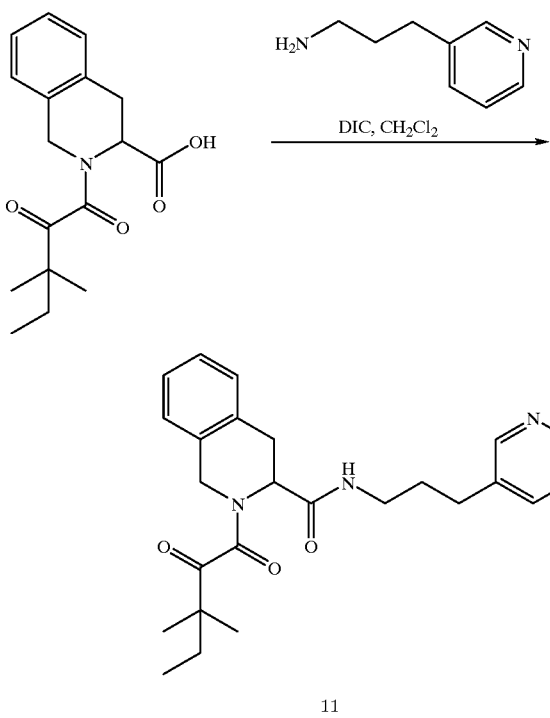

(3S)-2-(1,2-Dioxo-3-dimethy)pentyl-N-[3-(3-pyridyl)-1-propyl]-1,2,3,4-tetrahydro-3-isoquinolinecarboxamide To a solution of Reference Example 4 (0.25 g, 0.82 mmol) in methylene chloride (10 mL) was added diisopropylcarbodiimide (0.16 g, 1.3 mmol) and 3-(3-pyridyl)-1-propanol (0.16 g, 1.1 mmol) at about 25° C. under nitrogen. The solution was stirred at about 25° C. for about 20 h, then was filtered through Celite and concentrated. The crude residue was purified by silica gel column chromatography eluting with 3% methanol in methylene chloride to yield 0.05 g of product as a clear oil (15% yield). The NMR spectrum contains a doubling of resonances due to cis-trans amide rotamers. $^1$H NMR (CDCl$_3$) δ 0.95 (m, 3H); 1.22 (overlapping s's, 6H); 1.75 (m, 2H); 2.56 (m, 2H); 3.23 (m, 2H); 3.44 (m, 2H); 3.84 (m, 2H); 4.25–5.19 (overlapping m's, 3H); 7.22 (m, 5H); 7.46 (m, 1H); 8.43 (m, 2H).

REFERENCE EXAMPLE 20

4,5,6,7-Tetrahydrothienol[2,3-c]pyridine-5-carboxylic acid

A mixture of dl-β-(3-thienyl)alanine (5 g, 29.2 mmol) and formaldehyde (37%, 14.5 mL, 175 mmol) in 0.5 N H$_2$SO$_4$ (321 mL, 161 mmol) was stirred at about 25° C. for about 16 h. Water was evaporated and the residue was loaded on an ion-exchange column (strongly acidic DOWEX, 50WX2-200). The column was eluted with ethanol, water and ammonia sequentially. The ammonia fraction was lyophilized to give a yellow solid, 2.9 g (54% yield). $^1$H NMR (DMSO-d$_6$): δ 2.95 (m, 1H); 3.25 (m, 1H); 4.22 (m, 3H); 6.96 (d, J=7 Hz, 1H); 7.55 (d, J=7 Hz, 1H). MS (m/z): 184 (MH$^+$).

REFERENCE EXAMPLE 21

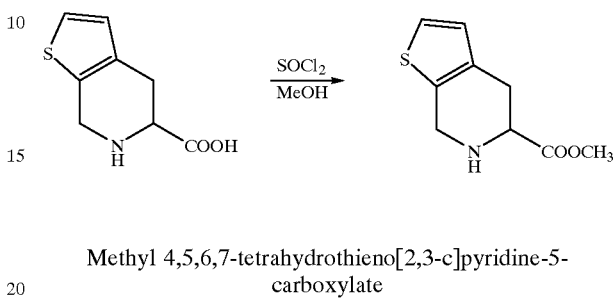

Methyl 4,5,6,7-tetrahydrothieno[2,3-c]pyridine-5-carboxylate

To a suspension of Reference Example 20 (300 mg, 1.64 mmol) in methanol (dry, 100 mL) HCl (1 N in ether) was added until the solid was dissolved. Thionyl chloride (683 mg, 5.7 mmol) was then added and the mixture was stirred at about room temperature for about 72 h. The mixture's pH was adjusted to about pH 12 with Na$_2$CO$_3$ and extracted with ethyl acetate. Purification by column chromatography (silica gel, ethyl acetate) gave a white solid; 103 mg (32% yield). MS (m/z): 196 (MH$^+$).

REFERENCE EXAMPLE 22

Methyl 6-(1,2-Dioxo-2-methoxyethyl)-4,5,6,7-tetrahydrothieno[2,3-c]pyridine-5-carboxylate To a solution of Reference Example 21 (102 mg, 0.515 mmol) in triethylamine (90 μL) and dichloromethane (anhydrous, 20 mL), methyloxalyl chloride was added at about 0° C. The mixture was stirred at about the same temperature for about 3 h. Water and ethyl acetate were added and the organic phase was washed with brine. After drying with MgSO$_4$ and evaporation of the solvent, column chromatography (silica gel, ethyl acetate) gave a colorless oil (138 mg, 95% yield). $^1$H NMR (CDCl$_3$) δ 3.05 (m, 1H); 3.36/3.42 (2s, 1H); 3.70 (2s, 3H); 3.92/3.94 (2s, 3H); 4.50/4.76 (2d, J=16 Hz, 1H); 4.88/4.27 (2d, J=16 Hz, 1H); 4.98/5.68 (2d, J=6 Hz, 1H); 6.79/6.81 (2d, J=7 Hz, 1H); 7.17/7.19 (2d, J=7 Hz, 1H). MS (m/z): 284 (MH$^+$).

REFERENCE EXAMPLE 23

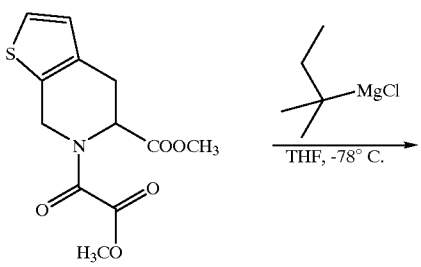

Methyl 6-(3,3-Dimethyl-1,2-dioxopentyl)-4,5,6,7-tetrahydrothieno[2,3c]pyridine-5-carboxylate To a solution of Reference Example 22 (80 mg, 0.283 mmol) in THF (anhydrous, 5 mL) 1,1-dimethylpropylmagnesium chloride (1.0 M in THF, 0.37 mL, 0.37 mmol) was added at about −78° C. The mixture was stirred at about −78° C. for about 3 h, quenched with NH$_4$Cl and extracted with ethyl acetate. Column chromatography (silica gel, 1:1 hexane:ethyl acetate) gave a colorless oil; 45 mg (49% yield). $^1$H NMR (CDCl$_3$): δ 0.909 (t, J=7 Hz, 3H); 1.25 (m, 6H); 1.75 (m, 2H); 3.03 (m, 1H); 3.36 (m, 1H); 3.69/3.70 (2s, 3H); 4.50/4.76 (2d, J=16 Hz, 1H); 4.60/5.68 (2d, J=6 Hz, 1H); 4.75/5.29 (2d, J=16 Hz, 1H); 6.79/6.81 (2d, J=7 Hz, 1H); 7.17/17.19 (2d, J=7 Hz, 1H). MS (m/z): 346 (M+Na$^+$).

REFERENCE EXAMPLE 24

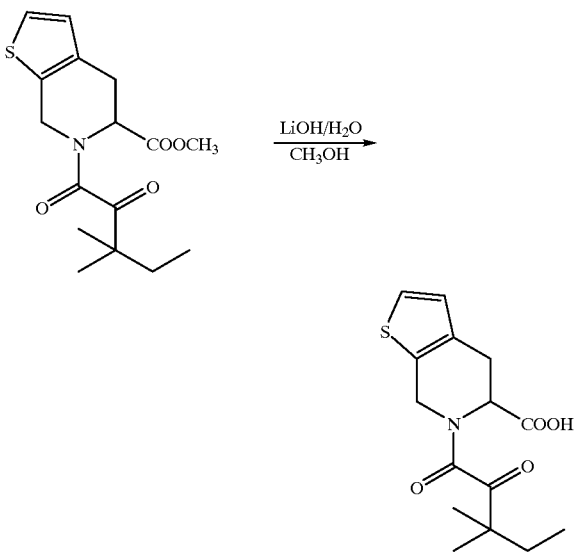

6-(3,3-Dimethyl-1,2-dioxopentyl)-4,5,6,7-tetrahydrothieno[2,3-c]pyridine-5-carboxylic acid A mixture of Reference Example 23 (42 mg, 0.1299 mmol) and LiOH (1N, 0.24 mL) in methanol (1.2 mL) was stirred at about room temperature for about 16 h, acidified with 1N HCl, extracted with ethyl acetate and dried with MgSO$_4$. After evaporation of the solvent and drying under vacuum a colorless oil was obtained (35 mg, 87% yield). $^1$H NMR (CDCl$_3$) δ 0.909 (t, J=7 Hz, 3H); 1.25 (m, 6H); 1.75 (m, 2H); 3.03 (m, 1H); 3.36 (m, 1H); 4.50 (d, J=16 Hz, 1H); 4.60/5.68 (2d, J=6 Hz, 1H); 4.75/5.29 (2d, J=16 Hz, 1H); 6.79/6.81 (2d, J=7 Hz, 1H); 7.17/7.19 (2d, J=7 Hz, 1H); 8.75 (br s, 1H). MS (m/z): 308 (M-1).

COMPOUND 12

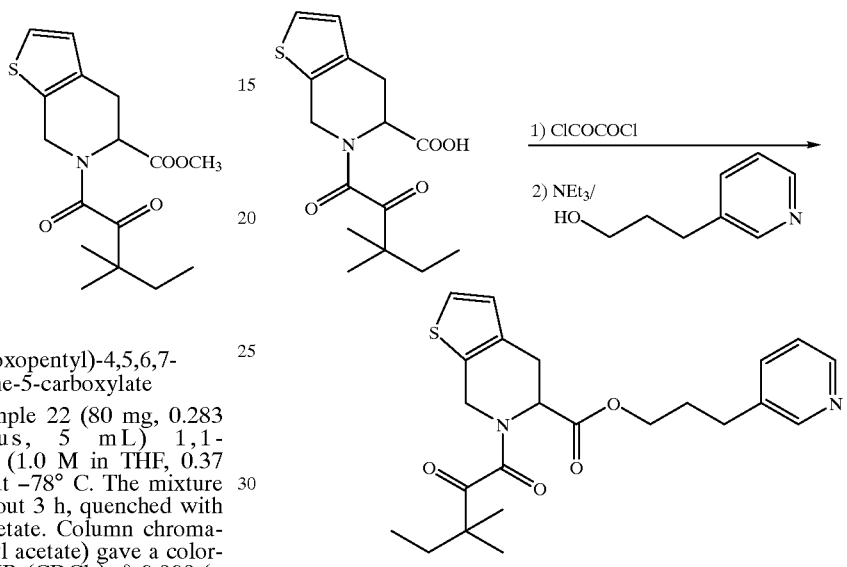

3-(3-Pyridyl)-1-propyl 6-(3,3-dimethyl-1,2-dioxopentyl)-4,5,6,7-tetrahydrothieno-[2,3-c]pyridine-5-carboxylic acid To a solution of Reference Example 24 (30 mg, 0.097 mmol) in dichloromethane (anhydrous, 2 mL) oxalyl chloride (1.0 M in dichloromethane, 0.116 mL, 0.116 mmol) and dimethylformamide (1 drop) were added. The mixture was stirred at about room temperature for about 3 h. Triethylamine (12 mg) and 3-(3-pyridyl)-1-propanol (13.2 mg, 0.097 mmol) were added and the mixture was stirred for about 5 h. Column chromatography (silica gel, 1:1 hexane:ethyl acetate) gave a colorless oil; (4.1 mg, 10% yield). $^1$H NMR (CDCl$_3$) δ 0.909 (t, J=7 Hz, 3H); 1.25 (m, 6H); 1.75 (m, 2H); 1.90 (m, 2H); 2.55 (m, 2H); 3.03 (m, 1H); 3.36 (m, 1H); 4.15 (m, 2H); 4.50 (d, J=16 Hz, 1H); 4.60/5.72 (2d, J=6 Hz, 1H); 4.75/5.29 (2d, J=16 Hz, 1H); 6.82/6.79 (2d, J=7 Hz, 1H); 7.20 (m, 2H); 7.39 (t, J=8 Hz, 1H); 8.36 (d, J=8 Hz, 1H); 8.45 (d, J=8 Hz, 1H). MS (m/z): 430 (MH$^+$).

IV. Biological Assays and Activity

Examples 1 and 4 in vitro activity results are shown in Table 2. Examples 2 and 3 detail the methods used for preparation of the cell cultures used in Example 4. Example 5 in vivo activity results are shown in FIG. 1.

A. In Vitro Biological Activity

EXAMPLE 1

Dorsal Root Ganglion (DRG) Culture

DRG are dissected from newborn or 1-day-old CD rats and placed into PBS on ice. After rinsing twice with sterile plating medium, DRG are transferred to empty wells of a 6-well plate coated with polyornithine/laminin (Becton Dickinson Labware) using #7 curved forceps. Three ml/well of plating medium are then added very gently, so as not to disturb the DRG. Plating medium is Leibovitz's L-15 medium (Gibco), plus 0.6% glucose, 33 mM KCl, 10% FCS, 10 mM Hepes and penicillin/streptomycin/glutamine. After overnight incubation at about 37° C. in 5% $CO_2$, this medium is replaced with 3 mL/well of assay medium [Leibovitz's L-15 medium plus 0.6% glucose, 1% FCS, 1% N-2 supplement (Gibco), 10 M ara-C, 10 mM Hepes, and penicillin/streptomycin/glutamine] containing either vehicle (DMSO, 1/200,000), positive control (24 ng/mL NGF) or test compound (50–250 nM). All media are prepared fresh daily. DRG are microscopically examined for neurite outgrowth on days 1–5. Under optimal conditions, vehicle treatment does not induce neurite outgrowth from DRG. An experiment is considered positive (+) if the instant compound induced neurites of ≧1 diameter of the DRG.

B. Cell Culture Assays

EXAMPLE 2

Primary Rat Hippocampal Cells

Hippocampal cells are dissected from the brains of embryonic day 18 rat pups and dissociated with trypsin (1 mg/mL) and trituration. Cells are seeded at 30,000 cells/well in 96-well plates filled with 100 μL MEM and 10% FBS. At 7 days in culture, cells are fixed with 4% paraformaldehyde and immuno-fluorescence is performed.

EXAMPLE 3

Human M17 Neuroblastoma Cells

M17 human neuroblastoma cells are cultured in 1:1 ratio of EMEM and Ham's F12 with 1×NEAA and 10% FBS. The culture media contains 1×PSN antibiotic and is exchanged every other day, and the cells are passed in log phase near confluence.

TABLE 2

In Vitro Neurotrophic Activity

| Cmpd | DRG | Rat Hippocampal Cell Response | M17 Cell Response |
| --- | --- | --- | --- |
| 1 | + | 155,124,115 | 113 |
| 2 | NT | NA | NA |
| 3 | NT | 122 | 106 |
| 4 | NT | 123 | NA |
| 5 | NT | 129 | 103 |
| 6 | NT | 143 | NA |
| 7 | NT | 117 | NT |
| 8 | NT | 109 | NA |
| 9 | NT | NA | NA |
| 10 | NT | 131 | NA |
| 11 | NT | 104 | NA |
| 12 | NT | 126 | NT |

+ = Positive results for each experiment
− = Negative results for each experiment
NA = Not active
NT = Not tested

EXAMPLE 4

Neurite Outgrowth Assay

Cultures are incubated with normal horse serum (1:50; Vector Labs) for about 20 min, rinsed and then incubated with primary antibody, microtubule associated-protein 2 (anti-mouse MAP-2; 1:1000; Chemicon) for about 2 h at about RT. Following primary antibody, cultures are rinsed and incubated with fluorescein anti-mouse IgG (rat absorbed; 1:50; Vector Labs) for about 1 h. After fluorescein incubation, the cultures are rinsed and read in PBS on a fluorescent plate reader (excitation: 485 nm; emission: 530 nm). A compound is regarded as active if the neurite outgrowth response is greater than the mean DMSO-treated control response on the same plate. The response to test compound is reported as percent of DMSO-treated control. The signal-to-noise separation is consistent: the fluorescence from DMSO control wells is at least two-fold greater than blank wells.

C. In Vivo Biological Activity

EXAMPLE 5

Rat Facial Nerve Compression Model

Long-Evans rats are anesthetized under ketamine (60 mg/kg)/xylazine (6 mg/kg). The facial nerve is exposed and mechanically compressed with forceps near the stylomastoid foramen unilaterally with the opposite, non-lesioned side serving as an internal control. Nerve compression causes paralysis of the whisker muscle, hence the reduced whisker movement on the lesioned side which is observed immediately after recovery from anesthesia. Rats received test compound p.o. at about 20 mg/kg twice a day for 15 days after the surgery. Control rats received vehicle only. Three to eight rats are tested in each group. Restoration of whisker movement after the treatment with compounds of the present invention is recorded at different post-operative time points daily, up to two weeks, and is shown in FIG. 1.

What is claimed is:
1. A compound of the formula:

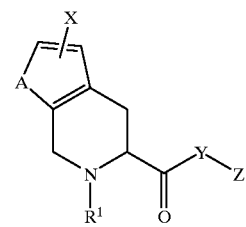

or a pharmaceutically acceptable salt thereof wherein (a) $R^1$ is selected from the group consisting of
  (i) $COCOR^2$, wherein $R^2$ is ($C_1$–$C_6$)-straight or branched alkyl, ($C_2$–$C_6$)-straight or branched alkenyl, ($C_5$–$C_7$)-cycloalkyl, 2-thienyl, 3-thienyl, phenyl, or substituted phenyl (the substituted phenyl ring having one to three substituents independently selected from the group consisting of lower alkyl, lower alkoxy, hydroxy and halogen),
  (ii) $CONHR^3$, wherein $R^3$ is ($C_1$–$C_6$)-straight or branched alkyl, and
  (iii) $SO_2R^4$, wherein $R^4$ is phenylalkyl or substituted phenylalkyl (the substituted phenyl ring having one to three substituents independently selected from the group consisting of lower alkyl, lower alkoxy, hydroxy and halogen);

(b) X is selected from the group consisting of hydrogen, lower alkyl, lower alkoxy, hydroxy and halogen;

(c) Y is O or NR$^5$, wherein R$^5$ is (C$_1$–C$_6$)-straight or branched alkyl;

(d) Z is cyclohexyl(C$_1$–C$_3$)alkyl, (C$_1$–C$_5$)-straight or branched alkyl or (C$_2$–C$_5$)-straight or branched alkenyl substituted in one or more positions with Ar, which Ar is selected from the group consisting of 2-pyridyl, 3-pyridyl, 4-pyridyl, phenyl and substituted phenyl (the substituted phenyl ring having from one to three substituents independently selected from the group consisting of lower alkyl, lower alkoxy, hydroxy and halogen), with the proviso that Z and R$^2$ cannot both be C$_1$-alkyl, and when Z is (C$_1$–C$_5$)alkyl, Ar is not phenyl; and (e) A is S or CH=CH.

2. The compound of claim 1, wherein Z is C$_3$-straight alkyl substituted in one or more positions with 3-pyridyl.

3. The compound of claim 1, wherein R$^1$ is COCOR$^2$, R$^2$ being C$_5$-branched alkyl.

4. The compound of claim 1, wherein A is CH=CH.

5. The compound of claim 1 having the structure

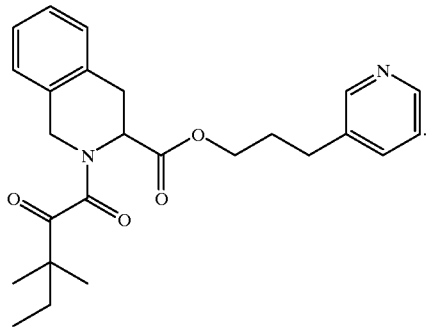

6. The compound of claim 1 having the structure

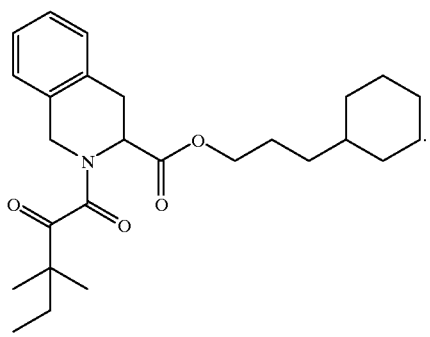

7. The compound of claim 1 having the structure

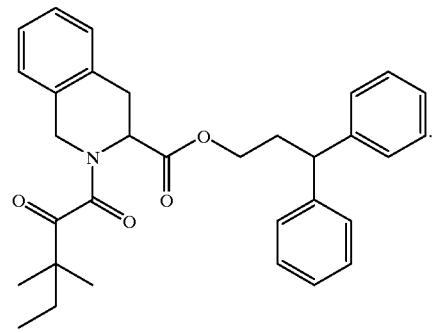

8. The compound of claim 1 having the structure

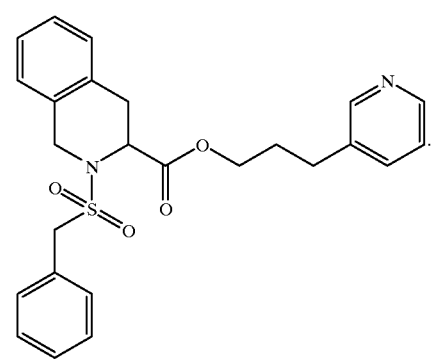

9. The compound of claim 1 having the structure

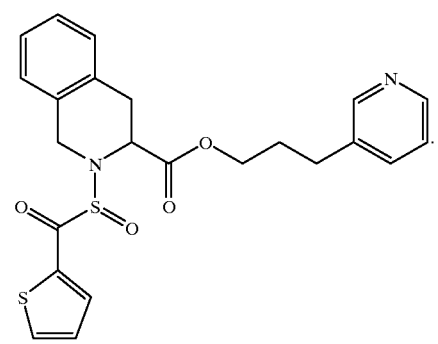

10. The compound of claim 1 having the structure

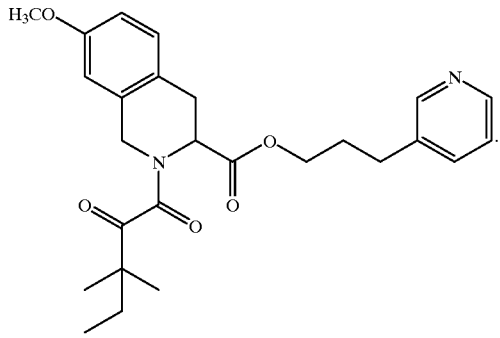

11. The compound of claim 1 having the structure

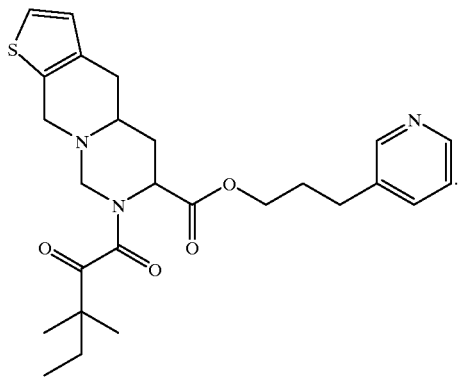

12. A method of stimulating neuronal growth in a subject afflicted with a disorder characterized by neuronal damage caused by disease or trauma comprising administering to the subject in need thereof a neurotropic effective amount of the compound of claim 1.

13. A pharmaceutical composition comprising the compound of claim 1 and a pharmaceutically acceptable carrier.

14. The method of claim 12, wherein the disorder is caused by disease, and is selected from the group consisting of Parkinson's disease, Alzheimer's disease, stroke, multiple sclerosis, amyotrophic lateral sclerosis, diabetic neuropathy and Bell's palsy.

15. The method of claim 12, wherein the disorder is caused by trauma to the brain, spinal cord or peripheral nerves.

* * * * *